United States Patent
Yamamori et al.

[11] Patent Number: 5,473,066
[45] Date of Patent: Dec. 5, 1995

[54] PROCESS FOR PREPARING BENZOTHIAZEPINE DERIVATIVES

[75] Inventors: Teruo Yamamori, Takarazuka; Hiroshi Harada, Toyonaka; Eiichi Oosugi, Kawanishi; Katsunori Sakai, Osaka, all of Japan

[73] Assignee: Shionogi & Co., Ltd., Osaka, Japan

[21] Appl. No.: 182,828

[22] Filed: Jan. 19, 1994

[30] Foreign Application Priority Data

Jan. 27, 1993 [JP] Japan .................... 5-011492

[51] Int. Cl.$^6$ ............... C07D 281/10; C07D 295/14; C07B 45/00
[52] U.S. Cl. ............... 540/491; 544/59; 544/160; 544/399; 546/221; 548/335.5; 548/375.1; 548/561; 548/569; 560/17; 562/431
[58] Field of Search ............... 540/491; 544/399, 544/160, 59; 546/221; 548/569, 561, 335.5, 375.1; 560/17

[56] References Cited

FOREIGN PATENT DOCUMENTS 2723192  5/1989  France .

OTHER PUBLICATIONS

Inoue, J. Med Chem 34, 675–687 (1991).
Nippon Chemical Co., Ltd. Chemical Abstracts, vol. 104, No. 11, 17 Mar. 1986 Abstract No. 88616e JP-A-60 146 884.
Higashigawa, Chemical Abstracts, vol. 101, No. 21, 19 Nov. 1984 Abstract No. 191353d JP-A-59 110 668.
Higashigawa, Chemical Abstracts, vol. 101, No. 19 5 Nov. 1984 Abstract No. 171294g JP-A-59 110 685.
Tanabe Seiyaku Co., Ltd., Chemical Abstracts, vol. 96, No. 5 1 Feb. 1982 Abstract No. 34905w JP-A-81 108 685.
Hashiyama et al., J. Chem., Soc. Perkin Trans. I 1984, pp. 1725–1732.
Hashiyama et al., J. Chem. Soc. Perkin Trans. I 1985, pp. 421–427.

*Primary Examiner*—Mark L. Berch
*Attorney, Agent, or Firm*—Wenderoth, Lind & Ponack

[57] ABSTRACT

Process for stereoselectivity preparing a cis-form of 5-(aminoalkylamino)-1,5-benzothiazepine derivative represented by formula (VI):

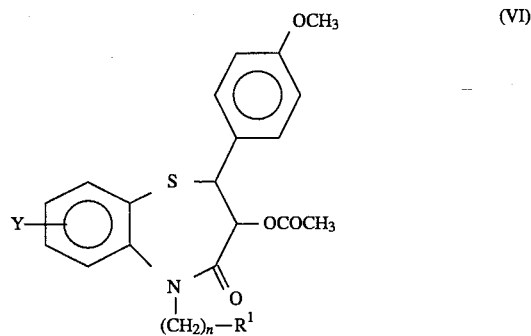

is provided, said process comprising carrying out a stereoselective addition reaction of an o-(aminoalkylamino) thiophenyl derivative with a trans-substituted glycidic ester at an elevated temperature in a nonpolar solvent in the presence of a divalent or trivalent iron ion to prepare a threo-form intermediate, hydrolyzing the ester group of said intermediate, acetylating the hydroxyl group of said hydrolyzed compound, and subjecting said acetylated compound to a ring closure reaction to obtain the objective compound (VI).

6 Claims, No Drawings

PROCESS FOR PREPARING BENZOTHIAZEPINE DERIVATIVES

BACKGROUND OF THE INVENTION (1) Field of the Invention

The present invention relates to a process for stereoselectively preparing cis-1,5-benzothiazepine derivatives, specifically a cis-form of 2-(4-methoxyphenyl)- 3-acetoxy-5-(aminoalkyl)-2,3-dihydro-1,5-benzothiazepin- 4(5H)-one represented by formula (VI):

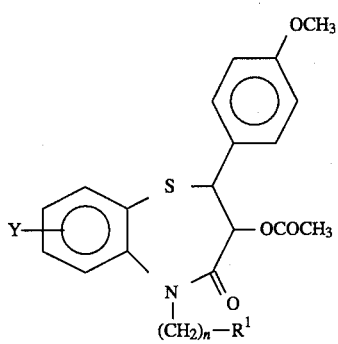

(VI)

wherein Y represents hydrogen, halogen, alkyl, alkoxy, aryl, arylalkyl, arylalkoxy or aryloxy; n is an integer of 1 to 6; and $R^1$ represents an amino group represented by the formula: $—NR^{1a}R^{1b}$ wherein $R^{1a}$ and $R^{1b}$ each independently represents hydrogen, straight or branched $C_1$–$C_6$ alkyl or aryl which can be substituted, or $R^{1a}$ and $R^{1b}$ may form, taken together with the nitrogen to which $R^{1a}$ and $R^{1b}$ are attached, a cyclic amino group which may be substituted or an aromatic heterocyclic group which may be substituted, provided that said cyclic amino group or said aromatic heterocyclic group may further contain one or more heteroatoms selected from the group consisting of nitrogen, oxygen and sulfur in the cyclic skeleton. The cis-1,5-benzothiazepine derivatives (VI) prepared by the process of the present invention are useful pharmaceutical compounds having a vasodilation action and a cardiac-muscle protecting action.

(2) Description of the Prior Art

As a process for preparing 1,5-benzothiazepine derivatives, an addition reaction of o-substituted thiophenol and epoxide is known (H, Kugita, H. Inoue, S. Takeo, Chem. Pharm. Bull., 18 2028 (1970); H. Inoue, S. Takeo, H. Kugita, Yakagaku Zasshi, 93 729 (1973)). As illustrated in reaction scheme 1, an o-aminothiophenol or o-nitrothiophenol derivative is reacted with an appropriately substituted glicidic ester to obtain an addition product. A ring closure of the product is then carried out through several steps to obtain compound (VII).

In the scheme, X represents hydrogen or oxygen; $R^2$ represents lower alkyl; and Y is as defined above.

When an o-nitrothiophenol derivative is used as a starting compound, the nitro group needs to be reduced to an amino group after the first step of the addition reaction. Compound (VII) can be converted to compound (VI) which is the objective compound of the present invention through further several steps (Reaction scheme 2) (Japanese patent application No. 302348/1991).

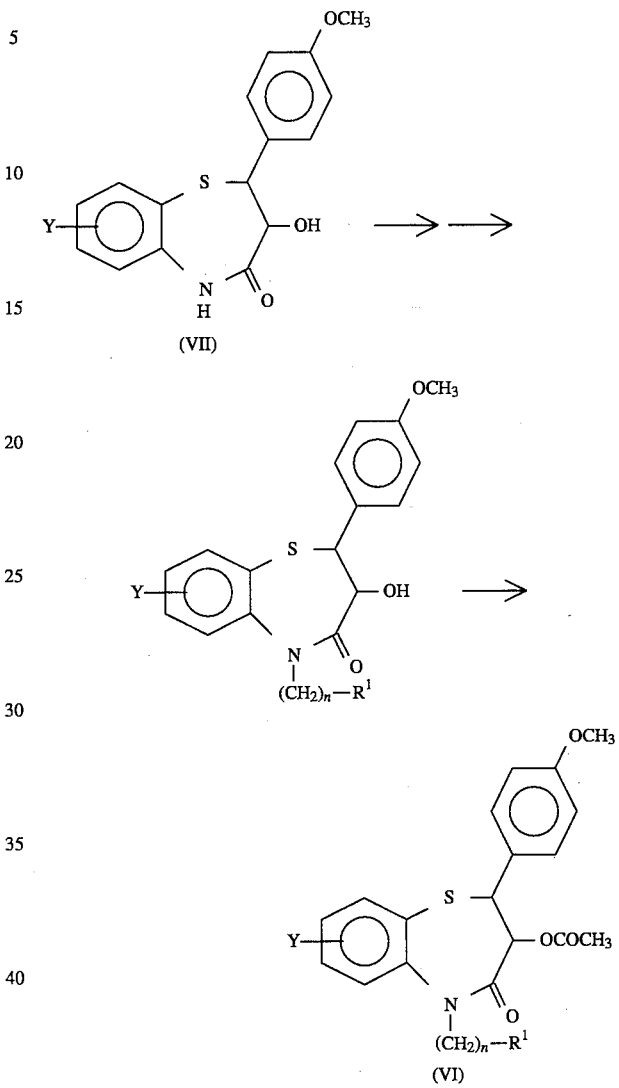

<Reaction scheme 2>

In the scheme, Y, n and $R^1$ are as defined above.

The stereochemistry (cis/trans) of compound (VI) or (VII) obtained by the process mentioned above directly reflects the stereoselectivity (threo/erythro) of the addition reaction of a substituted thiophenol and a trans-substituted glicidic ester (II). Because a cis-form of compound (VI), which is important as a medicine, is derived from a threo-form addition product, it has been desired to establish the reaction conditions and the chemical structure of starting substituted thiophenols which give stereoselectively a threo-form addition product in its reaction with compound (II).

It has been reported that o-nitrophenol derivatives stereoselectively react with compound (II) in the presence of a tin or zinc catalyst in an aprotic solvent to give a threo-form addition product (J. Med. Chem. 34, 675 (1991)). It is also known that an o-aminothiophenol derivative gives mainly a threo-form product in an aprotic solvent, while the same derivative gives as a main product an erythro-form in a polar solvent (see the above mentioned reference). However, effect of catalysts has not been investigated.

SUMMARY OF THE INVENTION

In order to obtain the intended cis-form of compound (VI) in high yield, the inventors of the present invention have established a novel synthesis route to compound (VI) and have investigated reaction conditions which maximize the stereoselectivity in the addition reaction of o-(aminoalkylamino) thiophenol derivatives (I) and trans-(4-methoxyphenyl) glicidic ester (II) which are starting compounds in the novel synthesis route.

The novel synthesis route to 1,5-benzothiazepine provided by the present invention is summarized in the following Reaction scheme 3.

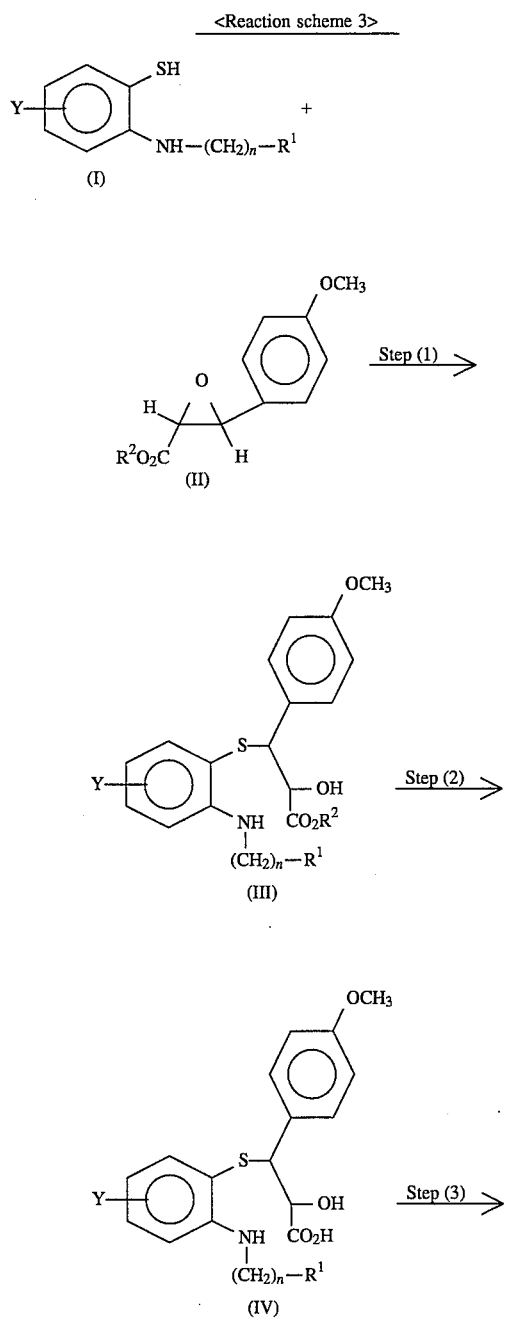

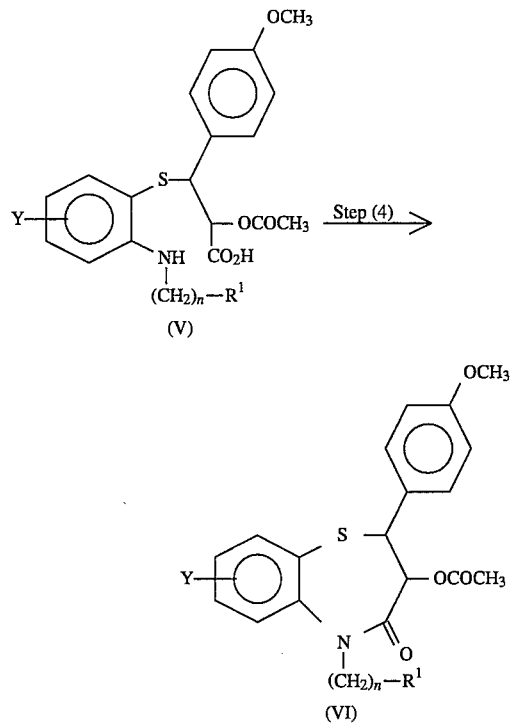

In the scheme, Y, n, $R^1$ and $R^2$ are as defined above.

Addition product (III) produced by Step (1) in the above reaction scheme 3 is converted to the intended compound (VI) through additional three steps. Since these steps proceed without racemization, the objective compound can also be obtained as an optically active compound, if an optically active compound is used as a starting compound (II).

The reaction conditions of the above Step (1) which determine the stereochemistry of the intended compound (VI) have been investigated, and it has become apparent that reaction solvent, reaction temperature and catalyst remarkably influence the stereoselectivity of this reaction. Thus, the inventors have found that the reaction at an elevated temperature in the presence of an iron catalyst in a nonpolar solvent is preferable in order to produce selectively a threo-form addition product ($III_T$) in high yield in Step (1).

The present invention provides a process for stereoselectivity preparing a cis-form of 1,5-benzothiazepine derivative represented by formula (VI):

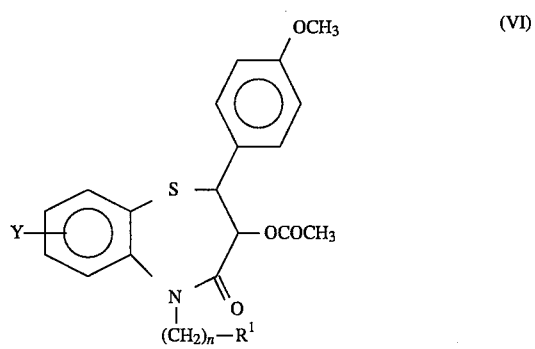

wherein Y represents hydrogen, halogen, alkyl, alkoxy, aryl, arylalkyl, arylalkoxy or aryloxy; n is an integer of 1 to 6; and $R^1$ represents an amino group represented by the formula: —$NR^{1a}R^{1b}$ wherein $R^{1a}$ and $R^{1b}$ each independently represents hydrogen, straight or branched $C_1$–$C_6$ alkyl or aryl which can be substituted, or $R^{1a}$ and $R^{1b}$ may form, taken together with the nitrogen to which $R^{1a}$ and $R^{1b}$ are attached, a cyclic amino group which may be substituted or an aromatic heterocyclic group which may be substituted, provided that said cyclic amino group or said aromatic heterocyclic group may further contain one or more heteroatoms selected from the group consisting of nitrogen, oxygen and sulfur in the cyclic skeleton, the process comprising, (1) stereoselectively preparing a threo-form of a compound represented by formula (III).

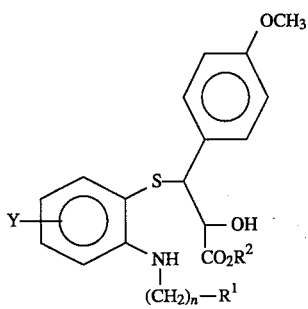

by reacting an o-(aminoalkylamino) thiophenol represented by formula (I):

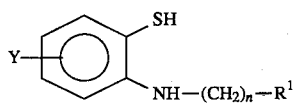

wherein Y, n and $R^1$ are as defined above, with a trans-3-(4-methoxyphenyl) glicidic ester represented by formula (II):

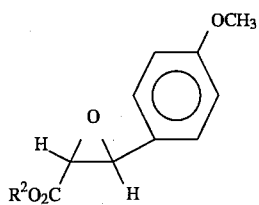

wherein $R^2$ represents lower alkyl, at an elevated temperature in a nonpolar solvent in the presence of a divalent or trivalent iron ion;

(2) hydrolysing the ester group of the compound obtained in Step (1) to yield a carboxylic acid represented by formula (IV):

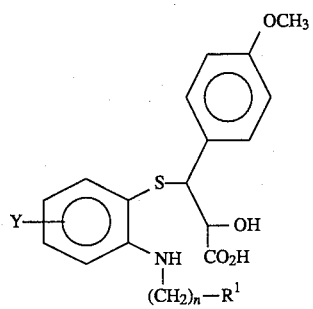

(3) acetylating the 2-hydroxyl group of the carboxylic acid obtained in Step (2) to convert it into a 2-acetoxy compound represented by formula (V):

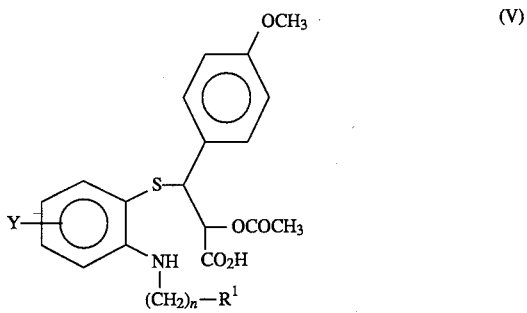

(4) subjecting the 2-acetoxy compound obtained in Step (3) to a ring closure reaction to convert it into a 1,5-benzothiazepine derivative represented by formula (VI).

In the present specification, the term halogen means fluorine, chlorine, bromine or iodine. Alkyl means straight or branched $C_1$–$C_6$ alkyl, and includes for example methyl, ethyl, n-propyl, isopropyl, n-butyl, isobutyl, secbutyl, tert-butyl, n-pentyl, isopentyl, neopentyl, tertpentyl, 2-metylbutyl, n-hexyl, isohexyl and the like, and $C_3$–$C_6$ cycloalkyl, for example, cyclopropyl, cyclobutyl, cyclopentyl, cyclohexyl and the like.

The term alkoxy means $C_1$–$C_6$ alkyloxy wherein the alkyl moiety is straight or branched, and includes for example methoxy, ethoxy, n-propoxy, i-propoxy, n-butoxy, i-butoxy, s-butoxy, t-butoxy, n-pentoxy, i-pentoxy, neopentoxy, s-pentoxy, t-pentoxy, n-hexyloxy, neohexyloxy, i-hexyloxy, s-hexyloxy, t-hexyloxy and the like.

Aryl means phenyl or naphthyl which may have one or more substituents including halogen, alkyl, alkoxy, hydroxyl, amino and the like.

In the definition of arylalkyl, arylalkoxy and aryloxy, the aryl moiety is as defined in the above definition of aryl, and the alkyl moiety is as defined in the above definition of alkyl.

Cyclic amino group means a 3 to 7 membered cyclic amino group which may have one or more atoms selected from the group consisting of nitrogen, oxygen and sulfur in the cyclic skeleton and includes for example 1-piperazinyl, 1-piperidyl, 1-pyrrolidinyl, 4-morpholinyl, 4-thiomorpholinyl and the like, all of which may have one or more substituents.

Aromatic heterocyclic group means a 5 to 6 membered aromatic heterocyclic group which may have one or more atoms selected from the group consisting of nitrogen, oxygen and sulfur in the cyclic skeleton and includes for example pyrrolyl, imidazolyl, pyrazolyl, pyridyl, pyridazinyl, pyramidinyl, pyrazinyl and the like, all of which may have one or more substituents.

As substituents in said cyclic amino group or said aromatic heterocyclic group, there are illustrated phenyl which may be substituted, $C_1$–$C_6$ alkyl, phenylalkyl which may be substituted, diphenylalkyl which may be substituted, heterocyclic group, —CO-heterocyclic group and the like. The substituents on substituted phenyl, phenylalkyl and diphenylalkyl include halogen, alkyl, alkoxy, methylenedioxy and the like. Said heterocyclic group means a saturated or unsaturated 5 to 6 membered ring which have one or more atoms selected from the group consisting of nitrogen, oxygen and sulfur and includes pyrrolyl, imidazolyl, pyrazolyl, pyridyl, pyridazinyl, pyrimidinyl, pyrazinyl, 1,3,5-triazinyl, 1,2,4-triazinyl, 1,2,3-triazinyl, isoxazolyl, oxazolyl, 1,2,3-oxadiazolyl, 1,2,4-oxadiazolyl, 1,2,5-oxadiazolyl, 1,3,4-oxadiazolyl, isothiazolyl, thiazolyl, 1,2,3-thiadiazolyl, 1,2,4-thiadiazolyl, 1,2,5-thiadiazolyl, 1,3,4-thiadiazolyl, furyl, thienyl and the like.

Each of the steps of the process of the present invention is described below.

Step (1)

In order to stereoselectively obtain the threo-form intermediate ($III_T$) in high yield, the reaction is carried out at an elevated temperature in the presence of an iron catalyst in a nonpolar solvent. Use of the nonpolar solvent, the iron catalyst and high reaction temperature are all advantageous in the production of the threo-form ester intermediate ($III_T$). The term "nonpolar solvent" in this specification means aromatic hydrocarbon, alicyclic hydrocarbon, or straight or branched hydrocarbon which may be substituted. Suitable nonpolar solvents for this reaction include, for example xylene, toluene, mesitylene, cymene, decalin, chlorobenzene, tetralin and the like. Xylene is particularly preferable. The term "iron catalyst" means inorganic or organic salts or complexes containing divalent or trivalent iron ions. Suitable iron catalysts for this reaction include, for example iron (III) hydroxide oxide, iron (III) chloride, iron (II) chloride, iron sulphate, iron (II) iodide, iron sulfide, iron 4-cyclohexylbutyrate, iron (III) oxide, iron (II) oxalate, iron (III) oxalate, iron (II) fluoride, iron (III) fluoride and the like. Iron (III) hydroxide oxide is particularly preferable.

Step (2)

The ester groups of the threo-form ester intermediate ($III_T$) and the erythro-form ester intermediate ($III_E$) obtained in Step (1) are hydrolyzed to obtain the corresponding threo-form carboxylic acid intermediate ($IV_T$) and erythro-form carboxylic acid intermediate ($IV_E$). This reaction is achieved by stirring for several hours at a temperature between ice-cooling and room temperatures in a water-containing polar solvent, for example, acetonitrile, tetrahydrofuran (THF), dioxane, ethanol, methanol, propanol, dimethylformamide (DMF), DMSO, HMPA and the like, using an equimolar amount to several-folds amount of a base such as sodium hydroxide, potassium hydroxide, barium hydroxide and lithium hydroxide. The threo-form carboxylic acid intermediate ($IV_T$) is isolated and purified by fractionating recrystalization of the mixed carboxylic acid intermediate ($IV_T/IV_E$) generated in this reaction. Alternatively, without isolating and purifying the threo-form carboxylic acid intermediate, the mixed carboxylic acid intermediate is used as such in the next acetylation step. Then, at any one of subsequent steps the intended threo-form or cis-form compound can be isolated and purified by known techniques such as recrystallization and column chromatography.

Step (3)

The 2-hydroxyl groups of the threo-form carboxylic acid intermediate ($IV_T$) or mixed carboxylic acid intermediate ($IV_T/IV_E$) obtained in Step (2) are acetylated to obtain the corresponding threo-form 2-acetoxy intermediate ($V_T$) or mixed 2-acetoxy intermediate ($V_T/V_E$). This reaction can be achieved by conducting the acylation using acetyl chloride or acetic anhydride in an organic solvent such as dichloromethane, chloroform, ethyl acetate, acetonitrile, toluene, THF and dioxane, in the presence of an organic and inorganic base such as pyridine, dimethylaminopyridine, triethylamine, N-methyl-morpholine, $NaHCO_3$ and $K_2CO_3$.

Step (4)

The threo-form 2-acetoxy intermediate ($V_T$) or mixed 2-acetoxy intermediate ($V_T/V_E$) obtained in Step (3) is subjected to a ring-closure reaction to obtain the intended 1,5-benzothiazepine derivative. The ring-closure reaction can be achieved using phosphoric anhydride, phosphorous halide, phosphorous oxyhalide, acetic anhydride or acyl halide, in an organic solvent such as dichloromethane, ethyl acetate, acetonitrile and THF, in the presence of an organic and inorganic base such as pyridine, triethylamine and $NaHCO_3$. The objective compound (VI) thus obtained can be isolated and purified by recrystallization or column chromatography on silica gel.

Starting compound (I) used in the above process of the present invention can be prepared by the known method (Yakugaku Zasshi 77, 347 (1956)) (Reaction scheme 4).

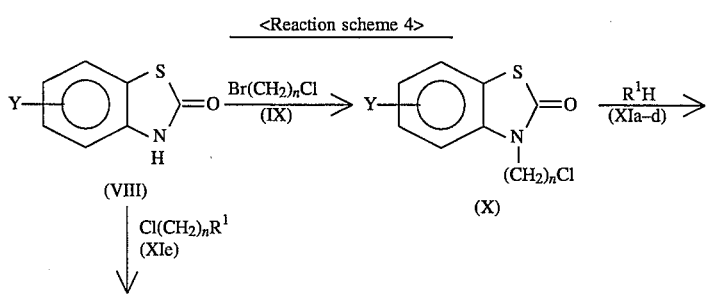

<Reaction scheme 4>

-continued
<Reaction scheme 4>

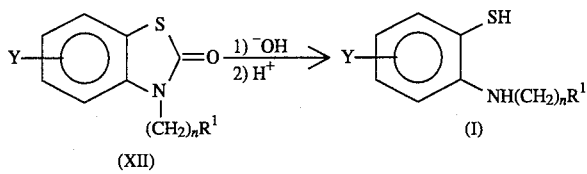

In the scheme, Y, n and $R^1$ are as defined above.

As previously mentioned, the advantages of the process of the present invention for preparing a cis-form of 1,5-benzothiazepine derivatives are the threo-stereoselectivity and the high yield of the reaction of Step (1). In order to demonstrate such advantages of the present invention, the effect of solvent, reaction temperature and catalyst on the stereochemistry and yield of the ester intermediate (III) produced in Step (1) are described below.

In order to examine the effects of solvent and reaction temperature on the stereochemistry and yield of the product, the yield and stereochemistry (threo/erythro ratio) of the products have been evaluated by carrying out the following reaction without catalyst in various solvents and at various temperatures (the reaction conditions other than catalyst, temperature and solvent were followed according to the description of Example 1). The results of the representative experiments are shown in Table 1.

TABLE 1

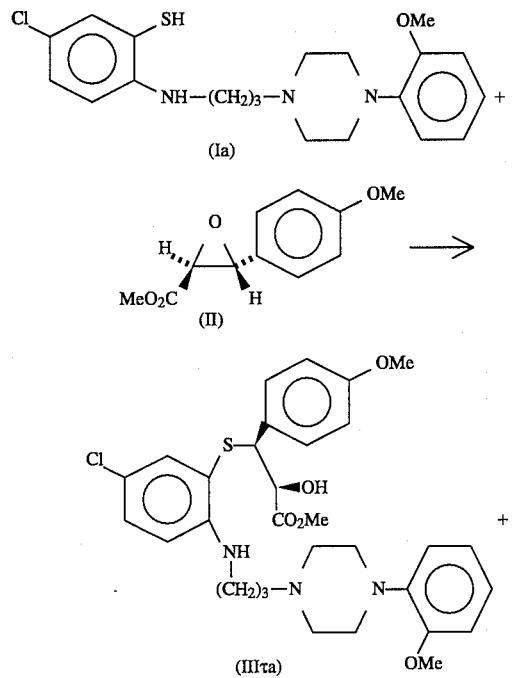

TABLE 1-continued

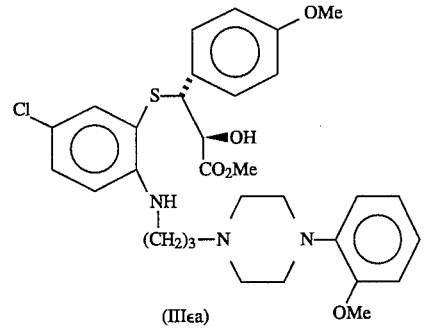

| Solvent | Temperature (°C.) | Yield (%)[1] ($III_Ta + III_Ea$) | Stereoselectivity[2] $III_Ta/III_Ea$ |
|---|---|---|---|
| Xylene | 50 | 87.1 | 0.01/1 |
| Xylene | 100 | 25.0 | 0.13/1 |
| Xylene | 142 | 61.8 | 3.41/1 |
| Mesitylene | 164 | 56.0 | 2.70/1 |
| Dioxane | 102 | 74.7 | 0.19/1 |
| DMF | 100 | 31.1 | 0.13/1 |
| Ethanol | 78 | 91.9 | 0.01/1 |

[1]See the footnote of Table 3.
[2]See the footnote of Table 3.

As can be seen from Table 1, this reaction proceeds in various solvents with relatively high yield. However, while the reactions in dioxane, DMF and ethanol give the threo/erythro ratio smaller than 0.2/1, the reactions carried out in a nonpolar solvent at an elevated temperature give an increased amount of the threo-form product, and particularly the reaction at reflux temperature gives the threo-form compound as the main product. Accordingly, in the process of the present invention which is directed to obtaining finally the cis-form of compound (VI), this reaction is most preferably carried out in a nonpolar solvent under reflux.

The Table 2 below shows the results of studies in which the effects of various metal catalysts were evaluated using the reaction condition under reflux in xylene which had showed the greatest value of threo/erythro ratio in the above experiments.

TABLE 2

| Catalyst (2 mg) | Yield (%)[1] $III_Ta + III_Ea$ | Stereoselectivity[2] $III_Ta/III_Ea$ |
|---|---|---|
| None | 61.8 | 3.41/1 |
| $AlCl_3$ | 41.3 | 1.44/1 |
| $BF_3 \cdot Et_2O$[a] | 23.3 | 2.42/1 |
| $CoF_3$ | 51.3 | 1.53/1 |
| $CuCl_2$ | 83.7 | 0.34/1 |
| $Mg(OH)_2$ | 52.8 | 3.05/1 |
| $MnO_2$ | 51.0 | 3.69/1 |
| $NiCl_2$ | 52.7 | 1.59/1 |
| $Ni(OH)_2$ | 52.8 | 3.15/1 |

TABLE 2-continued

| Catalyst (2 mg) | Yield (%)[1] III$_T$a + III$_E$a | Stereoselectivity[2] III$_T$a/III$_E$a |
| --- | --- | --- |
| PdCl$_2$ | 95.4 | 0.30/1 |
| RuCl$_3$ | 54.3 | 1.42/1 |
| SnCl$_2$.2H$_2$O | 56.5 | 1.10/1 |
| SnCl$_4$ | 54.2 | 1.64/1 |
| SnO$_2$ | 64.3 | 1.13/1 |
| TiCl$_4$ | 22.7 | 1.08/1 |
| Zn(OAc)$_2$.2H$_2$O | 72.1 | 0.50/1 |
| FeO(OH) | 83.1 | 7.62/1 |
| FeS | 77.7 | 5.94/1 |
| Fe(powder) | 58.8 | 3.20/1 |

[1]See the footnote of Table 3.
[2]See the footnote of Table 3.
[a]Amount of catalyst: 2 μl As can be seen from Table 2, the stereoselectivity of this reaction increases by using iron catalysts. Any of metal catalysts tested other than iron ion did not show significant catalytic actions or showed negative catalytic actions, i.e. the decrease of the threo/erythro ratio. The above mentioned reference (J. Med. Chem., 34, 675–687 (1991)) has reported that, in the reaction of an o-nitrothiophenol derivative with compound (II), only the erythro-form compound is produced in ethanol/benzene in the presence of sodium hydrogen carbonate, while a threo/erythro mixture containing the threo compound as a main product is produced in toluene in the presence of zinc acetate. On the contrary, in Step (1) in the present invention, zinc acetate showed a negative catalytic action and remarkably decreased the threo/erythro ratio.

Further, as can be understood from Table 2, iron powder does not show significant catalytic actions. Accordingly various iron catalysts containing divalent or trivalent iron ions can be used as the catalysts in this step.

The process of the present invention is specifically illustrated by the following examples. The symbols in the chemical formulae have the following means; Me: methyl group, Ac: acetyl group, Ph: phenyl group.

EXAMPLES

Example 1: Step (1)-a

The reaction of Step (1) described above was carried out using as starting compounds 5-chloro-2-[3-[4-(2-methoxyphenyl)piperazin- 1-yl]propyl]aminobenzenethiol (Ia) and methyl (−)-trans-3-(4-methoxyphenyl)glycidate in xylene in the presence of various iron catalysts. The representative example (Run 1) is described in detail below, and the results of a series of experiments conducted according to the procedure of Run 1 except for the use of different iron catalysts are summarized in Table 3.

Compound (Ia) (196 mg, 0.5 mmol), compound (II) (104 mg, 0.5 mmol) and iron (III) hydroxide oxide (2 mg) are added to dry xylene (3 ml) and refluxed for 1 hour. After cooling, the resulting reaction mixture is subjected to column chromatography on silica gel eluting with dichloromethane/ethyl acetate (1:1). The first eluate is recrystallized from ethyl acetate/hexane to obtain methyl (−)-erythro-3-[5-chloro-2-[3-[4-(2-methoxyphenyl)piperazin- 1-yl]propyl]aminophenylthio]-2-hydroxy-3-(4-methoxyphenyl)propionate (III$_T$a) (28.9 mg) as colorless prism-shaped crystals.

Yield: 9.7%.

Melting point: 168°–170° C.

Specific rotation: [α]$_D^{26}$=−39.2° (c=0.50, CHCl$_3$)

Elemental analysis: C$_{31}$H$_{38}$N$_3$O$_5$SCl. Calculated: C, 62.04; H, 6.38; N, 7.00. Found: C, 61.87; H, 6.34; N, 6.91.

IRvmax(nujol)(cm$^{-1}$): 3386, 3150, 1727.

NMR(CDCl$_3$)δ: 1.85(2H,m), 2.86(12H,m), 3.70(3H,S), 3.76(1H,d, J=4.6), 3.82(3H, S), 3.87(3H,S), 4.97(1H,d,d,J=8.2,4.6), 5.10 (1H,m), 6.49 (1H,d,J=9.0), 7.08 (10H,m).

The second eluate is converted into the oxalate which is recrystallized from ethyl acetate/ether to obtain oxalate of methyl (+)-threo-3-[5-chloro-2-[3-[4-(2-methoxyphenyl) piperazin-1-yl]propyl]aminophenylthio]-2-hydroxy- 3-(4-methoxyphenyl)propionate (III$_E$a) (220.4 mg) as colorless prism-shaped crystals.

Yield: 73.4%

Melting point: 123°–126° C.

Specific rotation: [α]$_D^{23.5}$=+108.4° (c=0.51, Methanol)

Elemental Analysis: C$_{31}$H$_{38}$N$_3$O$_5$SCl.2C$_2$O$_4$H$_2$. Calculated: C, 53.88; H, 5.43; N, 5.39. Found: C, 53.66; H, 5.40; N, 5.49.

IRvmax(nujol) (cm$^{-1}$) : 3430, 3358, 1728.

NMR (DMSO-d$_6$) δ: 1.93 (2H, m), 3.18 (12H, m), 3.45 (3H, S), 3.72 (3H, S), 3.79 (3H, S), 4.35 (1H,d,J=6.0), 4.40 (1H, d,J=6.0), 5.55 (NH, OH), 6.60 (1H,d,J=8.2), 7.02 (10H,m).

TABLE 3

| Run | Catalyst (2 mg) | Yield (%)[1] III$_T$a + III$_E$a | Stereoselectivity[2] III$_T$a/III$_E$a |
| --- | --- | --- | --- |
| 1 | FeO(OH) | 83.1 | 7.62/1 |
| 2 | FeO(OH)[a] | 81.4 | 7.62/1 |
| 3 | FeCl$_3$ | 69.1 | 4.08/1 |
| 4 | FeCl$_2$ | 71.6 | 5.10/1 |
| 5 | FeI$_2$ | 66.9 | 4.85/1 |
| 6 | FeS | 77.7 | 5.94/1 |
| 7 | Fe$_2$(OH)$_3$(C$_{10}$H$_{17}$O$_2$)$_3$[b] | 82.5 | 5.45/1 |
| 8 | Fe$_2$(SO$_4$)$_3$ | 71.4 | 4.95/1 |
| 9 | Fe$_2$O$_3$ | 63.8 | 4.46/1 |

[a]Amount of catalyst: 10 mg
[b]Ferric 4-cyclohexylbutyrate
[1]Isolated and purified as a mixture of III$_T$ and III$_E$ by silica gel column chromatography. III$_T$a: threo form, III$_E$a: erythro form.
[2]A threo/erythro ratio was determined by HPLC.
Column: COSMOSIL$_5$ C18 4.6 × 250 mm;
Mobile phase: acetonitrile/methanol/50 mM NaClO$_4$aq. (40/40/20);
Flow rate: 1.0 ml/min
Detection: UV254 nm
Retention time: III$_T$a(8.4,min), III$_E$a(9.6 min)

Example 2: Step (1)-b-e

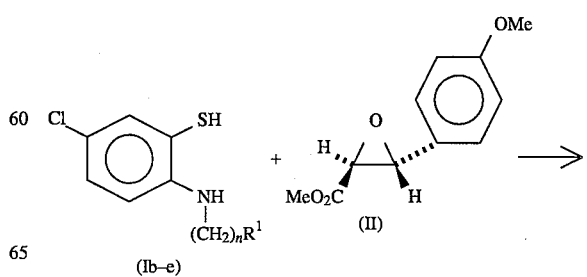

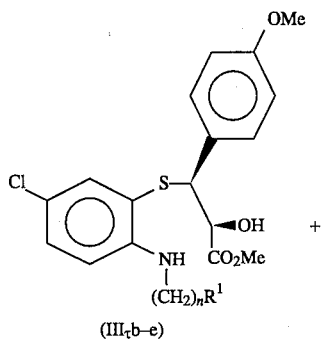

(III$_T$b–e)

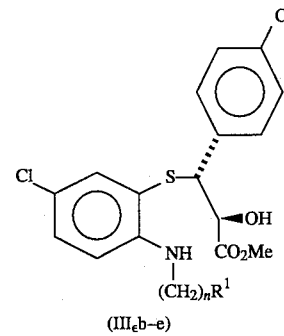

(III$_E$b–e)

The reaction of 5-chloro-2-N-(aminoalkyl)aminothiophenol (Ib-e) and methyl (−)-trans- 3-(4-methoxyphenyl)glycidate (II) was carried out according to the description in Example 1. The results are shown in Table 4.

TABLE 4

| Comp. No. | n | R¹ | Reaction condition[1] | | Yield (%)[2] | Stereoselectivity[3] |
|---|---|---|---|---|---|---|
| | | | Solvent | Catalyst | III$_T$ + III$_E$ | III$_T$/III$_E$ |
| b | 3 | −N⌒N−Ph | Xylene | Fe(O)OH | 93.6 | 8.62/1 |
| c | 3 | −N⌒N−C₆H₄−Me | Xylene | Fe(O)OH | 82.7 | 7.20/1 |
| d | 3 | −N⌒NCHPh₂ | Xylene | Fe(O)OH | 89.3 | 4.71/1 |
| e | 2 | −NMe₂ | Xylene | Fe(O)OH | 94.6 | 4.68/1 |

[1]Compound (Ib–e) (0.5 mmol), compound (II) (0.5 mmol) and catalyst (2 mg) were added to solvent (3 ml) and refluxed for 1 hour.
[2]The mixture of III$_T$b–e and III$_E$b–e was isolated and purified by column chromatography on silica gel.
[3]See the footnote in Table 3.

IR and NMR spectral data of compounds (III$_T$b-e) and (III$_E$b-e) produced by the above reactions are shown in Table 5.

TABLE 5

| Comp. No. | IRvmax(CHCl₃) (cm⁻¹) | NMR (CDCl₃) δ |
|---|---|---|
| III$_T$b | 3518, 3368, | 1.80(2H, q, J=6.6), 2.48(2H, t, |

TABLE 5-continued

| Comp. No. | IRvmax(CHCl₃) (cm⁻¹) | NMR (CDCl₃) δ |
|---|---|---|
| | 1738 | J=6.6), 2.64(4H, m), 3.17(6H, m), 3.60(3H, S), 3.77(3H, S), 3.89 (OH), 4.40(1H, d, J=3.0), 4.47 (1H, m), 5.27(NH), 6.53(1H, d, J=9.4), 6.74–7.38(11H, m). |
| III$_E$b | 3512, 3366, 1737 | 1.86(2H, q, J=6.6), 2.30(OH), 2.53(2H, t, J=6.6), 2.64(4H, m), 3.17(6H, m), 3.61(3H, S), 3.77 (3H, S), 4.34(2H, S), 5.65 (1H, NH), 6.57(1H, d, J=8.6), 6.73–7.45 (11H, m). |
| III$_T$c | 3512, 3366 1737 | 1.86(2H, q, J=6.6), 2.30(OH), 2.53(2H, t, J=6.6), 2.64(4H, m), 3.17(6H, m), 3.61(3H, S), 3.77 (3H, S), 4.34(2H, S), 5.65(NH), 6.57(1H, d, J=8.6), 6.73–7.45 (11H, m). |
| III$_E$c | 3514, 3364, 1738 | 1.86(2H, q, J=6.6), 2.27(3H, S), S), 2.58(4H, m), 2.54(2H, t, J=36.6), 3.13(7H, m), 3.60(3H, S), 3.77(3H, S), 4.33(2H, S), 6.57 (1H, d, J=8.6), 6.74–7.44(10H, m) |
| III$_T$d | 3516, 3366, 1737 | 1.7(2H, m), 2.20–2.40(10H, m), 3.08(2H, m), 3.43(OH), 3.59(3H, S), 3.76(3H, S), 4.19(1H, S), 4.37 (1H, d, J=3.2), 4.45(1H, m), 5.18 (NH), 6.49(1H, d, J=9.4), 6.83 (2H, d, J=8.6), 6.93–7.46(14H, m) |
| III$_E$d | 3518, 3368, 1736 | 1.80(2H, q, J=6.8), 2.20–2.75 (10H, m), 3.03(OH), 3.12(2H, t, J=6.8), 3.59(3H, S), 3.76(3H, S), 4.18(1H, S), 4.32(2H, S), 5.57 |
| III$_T$e | 3340, 1744 | (NH), 6.53(1H, d, J=8.8), 6.79 (2H, d, J=8.8), 7.09–7.47(14H, m) 2.35(6H, S), 2.68(2H, m), 3.26 (2H, m), 3.42(3H, S), 3.65(OH), 3.79(3H, S), 4.18(1H, d, J=8.0), |

TABLE 5-continued

| Comp. No. | IRvmax(CHCl$_3$) (cm$^{-1}$) | NMR (CDCl$_3$) δ |
|---|---|---|
| III$_E$e | 3356, 1744 | 4.27(1H, d, J=8.0), 5.85(NH), 6.47(1H, d, J=9.0), 6.79(2H, d, J=8.8), 6.84(1H, d, J=2.2), 7.04 (2H, d, J=8.8), 7.16(1H, d, d, J=2.2, 9.0). 2.30(6H, S), 2.63(2H, m), 3.02 (OH), 3.3(2H, m), 3.53(3H, S), 3.78(3H, S), 4.14(1H, d, J=3.2), 4.41(1H, d, J=3.2), 6.08(NH), 6.50(1H, d, J=8.8), 6.83(2H, d, J=8.8), 7.20(1H, d, J=2.6, 8.8), 7.42(2H, d, J=8.8), 7.56(1H, d, J=2.6). |

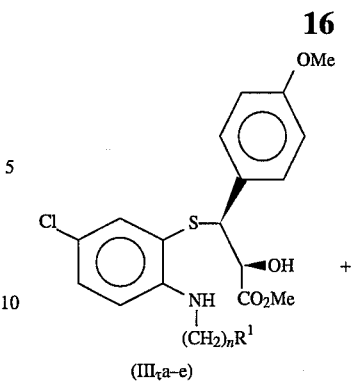

(III$_T$a–e)

Reference Example 1

In order to further study the effects of solvent and catalyst in Step (1) in the process of the present invention, each of the reactions described in Example 2 was carried out using a different solvent and/or catalyst and the respective yields and stereoselectivities were evaluated. The results are described in Table 6.

TABLE 6

| Comp. No. | n | R$^1$ | Reaction condition[1] Solvent | Catalyst | Yield (%)[2] III$_T$ + III$_E$ | Stereoselectivity[3] III$_T$/III$_E$ |
|---|---|---|---|---|---|---|
| b | 3 | —N⏜N—⌬ | Ethanol | — | 89.2 | 0.01/1 |
| c | 3 | —N⏜N—⌬—Me | Ethanol | — | 84.9 | 0.01/1 |
| d | 3 | —N⏜NCHPh$_2$ | Ethanol | — | 89.6 | 0.09/1 |
| e | 2 | —NMe$_2$ | Xylene | Zn(OAc)$_2$ | 66.7 | 1.57/1 |
|   |   |   | Xylene | — | 76.9 | 1.58/1 |
|   |   |   | Ethanol | — | 86.3 | 0.02/1 |

[1]Compound (Ib–e) (0.5 mmol), compound (II) (0.5 mmol) and catalyst (2 mg) were added to solvent (3 ml) and refluxed for 1 hour.
[2]The mixture of III$_T$b–e and III$_E$b–e was isolated and purified by column chromatography on silica gel.
[3]See the footnote in Table 3.

It can be seen by comparing the results in Table 4 with those in Table 6 that even if a substituent having a different structure (R$^1$—(CH$^2$)n—) is located at the 5-position in the starting compound (I), the reaction condition in which the reaction mixture is refluxed in nonpolar solvent in the presence of iron catalyst is the most advantageous condition for production of the desired threo-form compound (III$_T$).

In the following Examples 3~7, Step (2) in the process of the present invention is illustrated.

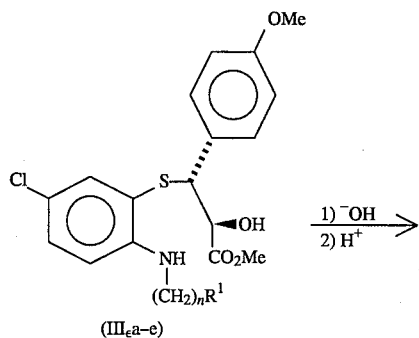

(III$_\epsilon$a–e)

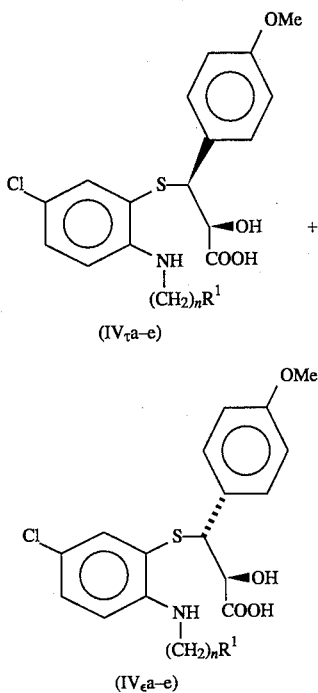

(IV$_T$a-e)

(IV$_E$a-e)

Example 3: Step (2)-a

Methyl 3-[5-chloro-2-[3-[4-(2-methoxyphenyl)piperazin-1-yl]propyl]aminophenyl thio]-2-hydroxy-3-(4-methoxyphenyl) propionate(III$_T$a+III$_E$a, threo/erythro=6.3/1) (131.9 g, 0.21 mol) is dissolved in acetonitrile (800 ml) and a solution of NaOH (8.4 g, 0.21 mol) in water (200 ml) is added. The resulting mixture is stirred at room temperature for 5 hours and evaporated in vacuo. The alkaline aqueous layer is neutralized to pH 4 with acetic acid and the product is crystallized by adding ethyl acetate. The precipitated crystals are filtered off, washed with water and dried to obtain crude crystals (100 g, yield=79%, threo/erythro=7.33/1). The resulting crystals are recrystallized from water-containing acetone to obtain the crystals (IV$_T$a+IV$_E$a, 85.6 g, yield =67.8%, threo/erythro=11.5/1 (HPLC)). This product is several times recrystallized from ethanol to obtain (+)-threo-3-[5-chloro- 2-[3-[4-(2-methoxyphenyl)piperazin-1-yl]propyl] aminophenyl thio]-2-hydroxy-3-(4-methoxyphenyl)propionic acid (IV$_T$a) (purity=100%) as colorless needle-shaped crystals.

HPLC: Column, COSMOSIL$_5$C18 4.6×250 mm

Mobile phase :acetonitrile/PICB-7 aqueous solution (50/50)

Flow rate: 1.0 ml/min

Detect ion: UV254 nm

Retention time: IV$_T$a (6.5 min), IV$_E$a (6.2 min)

Melting point: 108°–110° C.

Specific rotation: $[\alpha]_D^{24}$=+368.2°(c=1.004 Methanol)

Elemental analysis: C$_{30}$H$_{36}$N$_3$O$_5$SCl.½H$_2$O. Calculated:C, 60.54 ;H, 6.26 ;N, 7.06. Found: C, 60.36 ;H, 6.32 ;N, 7.13.

IRvmax(nujol) (cm$^{-1}$) :3332,1725

NMR (CDCl$_3$) δ:2.25 (2H,m), 2.82–3.67 (12H,m), 3.79 (3H, S), 3.88(3H, S), 3.37 (2H, m), 5.10 (3H), 6.44 (1H, d,J=8.6), 6.77–7.44 (10H,m).

Reference example 2

The reaction of Example 3 was carried out using the mixture containing erythro-form compound (III$_E$a) as a main component. The results are shown below.

3-[5-Chloro-2-[3-[4-(2-methoxyphenyl)piperazin-1-yl]propyl]aminophenylthio]-2-hydroxy-3-(4 -methoxyphenyl)propionic acid (III$_T$a+III$_E$a, threo/erythro= 0.01/1, 391 mg, 0.65 mmol) was dissolved in THF (4 ml) and 1N NaOH (0.65 ml) was added. The resulting mixture was stirred for 3 hours and neutralized with acetic acid (0.5 ml), and water was added. The resulting mixture was extracted with ethyl acetate. The layer of ethyl acetate is dried over MgSO$_4$. The solvent was distilled away to obtain (−)-erythro-3-[5-chloro-2-[3-[4-(2-methoxyphenyl)piperazin- 1-yl]propyl]aminophenyl thio]-2-hydroxy- 3-(4-methoxyphenyl)propionic acid (IV$_E$a) (355 mg, yield=93.1%) as an oil.

MS :m/e, 586 (MH+)

Specific rotation: $[\alpha]_D^{24}$=−61.3°(c=1.005 DMSO)

IRvmax (CHCl$_3$) (cm$^{-1}$): 3488,3352,1690.

NMR(DMSO-d$_6$) δ:1.74 (2H,m),2.40 (4H,m),3.0 (8H,m), 3.35 (2H), 3.69 (3H, S),3.76(3H, S),3.82(1H,d,J=2.4), 4.44(1H,d,J=2.4),5.76 (NH),6.45–7.34(11H,m).

Example 4: Step. (2)-b

The reaction is carried out using methyl 3-[5-chloro-2-[3-(4-phenylpiperazin-1-yl)propyl]aminophenylthio]-2-hydroxy- 3-(4-methoxyphenyl)propionate (III$_T$b+III$_E$b, threo/erythro= 8.62/1) (2.22 mg, 4.0 mmol) in a similar manner to that described in Example 3 to obtain carboxylic acid intermediate (IV$_T$b+IV$_E$b, threo/erythro=8.1/1 (NMR), 1.95 g, yield=87.4%) in an amorphous form.

Spectral data for IV$_T$b:

IRvmax(CHCl$_3$) (cm$^{-1}$) :3348,1712.

NMR(CDCl$_3$) δ:2.25 (2H,m),2.96–3.72 (12H,m),3.79 (3H,S), 4.36(2H, S),5.68(3H),6.44(1H,d,J=9.0), 6.76–7.44(11H,m).

Example 5: Step (2)-c

Methyl threo-3-[5-chloro-2-[3-[4-(4-methylphenyl) piperazin-1-yl]propyl]aminophenylthio]-2-hydroxy-3-(4-methoxyphenyl)propionate (III$_T$c) (753 mg, 1.29 mmol) is treated in a similar manner to that described in Example 3 to obtain carboxylic acid intermediate (IV$_T$c) (707 mg, yield=96.2%) in an amorphous form.

IRVvmax(CHCl$_3$)(cm$^{-1}$):3348,1713.

NMR (CDCl$_3$)δ:2.07 (3H, S), 2.27 (2H,m), 2.80–3.72 (12H,m), 3.78(3H,S),4.36(2H,m),6.17(3H),6.44(1H,d,J= 8.6),6.76–7.42 (10H,m).

Example 6: Step. (2)-d

Methyl threo-3-[5-chloro-2-[3-(4-benzhydryl)piperazin-1-yl]propyl]aminophenyl thio]-2-hydroxy-3-(4-methoxyphenyl) propionate (III$_T$d+III$_E$d, threo/erythro=4.71/1) (3.73 mg, 5.65 mmol) is treated in a similar manner to that described in Example 3 to obtain carboxylic acid intermediate (IV$_T$d+ IV$_E$d, threo/erythro=4.75/1 (NMR)) (3.42 g, yield=93.7%) in an amorphous form.

Spectral data for IV$_T$d:

IRvmax(CHCl$_3$)(cm$^{-1}$):3348,1712.

NMR (CDCl$_3$) δ: 1.90–3.40 (14H, m), 3 . 79 (3H, S), 4.31 (1H, S), 4.35 (2H,S), 6.15 (3H), 6.40 (1H,d,J=8.8), 6.81 (2H,d,J=8.8), 6.95 (1H, d J=2.6),7.03–7.50(13H,m).

Example 7: Step (2)-e

Methyl threo-3-[5-chloro-2-[(2-dimethylamino)ethyl]aminophenylthio]-2-hydroxy-3-(4-methoxyphenyl)propionate (III$_T$e) (0.476 mg, 1.084 mmol) is treated in a similar manner to that described in Example 3 and the product is recrystallized from dichloromethane/methanol to obtain carboxylic acid intermediate (IV$_T$e) (395 mg, yield=85.7%) as colorless prism-shaped crystals.

Melting point : 206°–208° C.

Specific rotation: $[\alpha]_D^{24}$=+472.5°(C=0.502, Methanol)

Elemental analysis: $C_{20}H_{25}N_3O_4SCl\cdot\frac{1}{2}H_2O$.

Calculated: C, 56.05 ;H, 5.97 ;N, 6.54.

Found: C, 56.01;H, 5.93 ;N, 6.58.

IRvmax(nujol) (cm$^{-1}$) :3260,2346,1609.

NMR(DMSO-d$_6$)δ:2.79(6H,S),3 .30(6H,m),3.75(3H,S), 3.95(1H,d, J=1.2), 4.09 (1H,d,J=1.2), 5.75 (NH), 6.69 (1H, d,J=9.0), 6.87 (2H, d, J=8.8),6.88(1H,d,J=2.8),7.22(1H,d,d, J=2.8,9.0),7.30(2H,d,J =8.8).

Reference example 3

Methyl erythro-3-[5-chloro-2-[(2-dimethylamino)ethyl]aminophenylthio]-2-hydroxy-3-(4-methoxyphenyl)propionate (III$_E$e) (439 mg, 1 mmol) is treated in a similar manner to that described in Example 3 and the product is recrystallized from methanol to obtain carboxylic acid (IV$_E$e) (298 mg, yield=70.1%) as colorless prism-shaped crystals.

Melting point:162°–164° C.

Specific rotation:$[\alpha]_D^{29}$=−310.2(c=0.509 Methanol)

Elemental analysis:$C_{20}H_{25}N_2O_4SCl$. Calculated:C, 56.53;H,5.93;N,6.59. Found: C, 56.32 ;H, 5.98 ;N, 6.55.

IRvmax (nujol) (cm$^{-1}$): 3342,1607.

NMR(DMSO-d6)δ:2.50(6H,S),2.87(2H,m),3.31(2H,m), 3.72(3H, S), 3.98 (1H,d,J=5.4),4.20 (1H,d,J=5.4),4.33 (2H), 5.96 (NH),6.66 (1H,d,J=8.6), 6.81 (2H,d,J=9.0), 7.11 (1H, d,j=2.6), 7.20 (1H,d,d, J=2.6,8.6), 7.23 (2H,d,J=9.0).

Step (3) in the process of the present invention is illustrated in the following Examples 8–12.

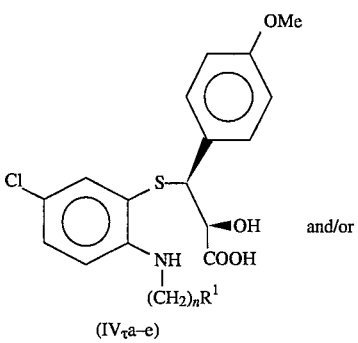

(IV$_\tau$a–e)

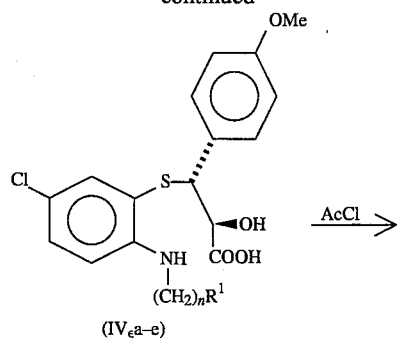

(IV$_\epsilon$a–e)

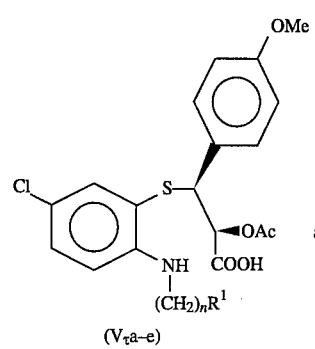

(V$_\tau$a–e)

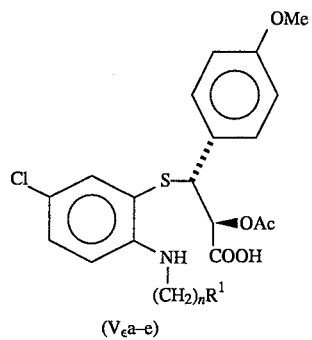

(V$_\epsilon$a–e)

Example 8: Step (3)-a

Threo-3-[5-chloro-2-[3-[4-(2-methoxyphenyl)piperazin-1-yl]propyl]aminophenylthio]-2-hydroxy-3-(4-methoxyphenyl) propionic acid (IV$_T$a) (117 mg, 0.2 mmol) and pyridine (39 μl, 0.48 mmol) are dissolved in dichloromethane (4 ml) and a solution of acetyl chloride (17 μl, 0.24 mmol) in dichloromethane is added dropwise over 5 minutes under ice-cooling. The resulting reaction mixture is stirred under ice-cooling for 30 minutes, poured into ice, and then extracted with ethyl acetate. The layer of ethyl acetate is washed with a saturated saline solution, dried over magnesium sulfate and filtered. Threo-2-acetoxy intermediate (V$_T$a) (118 mg, yield=94.4%) is obtained in an amorphous form from the filtrate.

HPLC:Column, TSKgel ODS 120T 4.6×250 mm.

Mobile phase:acetonitrile/PICB-7 aqueous solution (60/40)

Flow rate:1.0 ml/min

Detection:UV254 nm

Retention time:6.6 min

IRvmax(CHCl$_3$)(cm$^{-1}$):3340,2392,1736,1608.

NMR (CDCl$_3$) δ: 2.20 (3H, S), 2.22 (2H, m), 2.70–3.60 (12H, m), 3.73 (2H),3.80 (3H,S),3.87 (3H,S),4.49 (1H,d,J=

2.0),5.31 (1H,d, J=2.0), 6.45 (1H,d,J=8.6), 6.76–7.15 (8H, m), 7.33 (2H,d,J=8.6).

Reference example 4

Erythro-3-[5-chloro-2-[3-[4-(2-methoxyphenyl)piperazin-1-yl]propyl]aminophenylthio]-2-hydroxy-3-(4-methoxyphenyl)propionic acid ($IV_E$a) (625 mg, 1.066 mmol ) and pyridine (0.21 ml, 2.6 mmol ) are added to dichloromethane (2.5 ml), and 1N solution of acetyl chloride in dichloromethane (1.28 ml) is added dropwise over 5 minutes. The resulting reaction mixture is stirred under ice-cooling for 30 minutes, poured into ice water and extracted with ethyl acetate. The organic layer is washed with saline saturated solution and dried over $MgSO_4$ to obtain 2-acetoxy compound ($V_E$a) (662 mg, yield=98.8%) in an amorphous form from the filtrate.

HPLC: Column, $COSMOSIL_5$ C18.

Retention time: 3.7 min ($V_E$a)

IRvmax($CHCl_3$) ($cm^{-1}$) :3348,1734.

NMR ($CDCl_3$) δ:2.03 (2H,m), 1.98 (3H, S), 2.85–3.50 (12H,m), 3.68 (3H, S), 3.84 (3H,S), 4.40 (1H, d,J=8.8), 5.35 (1H, d,J=8.8), 6.43 (1 d, J=8.6),6.74(2H,d,J=8.6), 6.81–7.20(8H,m),7.50(2H).

Example 9: Step (3)-b

3-[5-Chloro-2-[3-(4-phenylpiperazin-1-yl)propyl] aminophenylthio]-2-hydroxy-3-(4-methoxyphenyl)propionic acid ($IV_T$b+$IV_E$b, threo/erythro=8.1/1) (1.945 g, 3.497 mmol) is acetylated in a similar manner to that described in Example 8 to obtain 2-acetoxy intermediate ($V_T$b+$V_E$b, threo/erythro=8.62/1 (NMR)) (2.006 g, yield=95.9%) in an amorphous form.

Spectral data for $V_T$b:

IRvmax($CHCl_3$)($cm^{-1}$):3346,1736.

NMR ($CDCl_3$) δ:2.21 (2H, m), 2.19 (3H, S), 2.98–3.64 (12H, m), 3.79 (3H, S),4.47 (1H,d,J=2.0),5.15 (2H),5.29 (2H,d,J=2.0), 6.45 (1H,d, J=8.6),6.77–7.38(11H,m).

Example 10: Step (3)-c

Threo-3-[5-chloro-2-[3-[4-(4-methylphenyl)piperazin-1-yl] propyl]aminophenyl t hi o]-2-hydroxy -3-(4-methoxyphenyl) propionic acid ($IV_T$c) (707 mg, 1.24 mmol) is acetylated in a similar manner to that described in Example 8 to obtain 2-acetoxy intermediate ($V_T$c) (722 mg, yield=95.1%) in an amorphous form.

IRvmax($CHCl_3$) ($cm^{-1}$) :3340,1737.

NMR ($CDCl_3$) δ: 2.18 (2H, m), 2.19 (3H, S), 2.28 (3H, S), 2.98–3.60 (12H,m), 3.79 (3H,S), 4.48 (1H,d,J=2.2), 5.29 (1H,d,J=2.2), 6.45 (1H,d,J=8.6), 6.74–7.37 (10H,m), 8.10 (2H).

Example 11: Step (3)-d

3-[5-Chloro-2-[3-(4-benzhydrylpiperazin-1-yl)propyl] aminophenylthio]-2-hydroxy-3-(4-methoxyphenyl)propionic acid ($IV_T$d+$IV_E$d, threo/erythro=4.75/1),(3.423 g, 5.297 mmol) is acetylated in a similar manner to that described in Example 8 to obtain 2-acetoxy intermediate ($V_T$d+$V_E$d, threo/erythro=4.75/1 (NMR)) (3. 352 g, yield=91.9%) in an amorphous form.

Spectral data for $V_T$d:

IRvmax ($CHCl_3$) ($cm^{-1}$): 3342,1735.

NMR: ($CDCl_3$) δ:2.1(2H,m),2.19(3H,S),2.34–3.37(12H, m),3.79 (3H, S), 4.32 (1H,S), 4.47 (1H,d,J=2.0), 5.30 (1H, d,J=2.0), 6.25 (2H), 6.41(1H,d,J=8.6),6.75–7.46(16H,m).

Example 12: Step. (3)-e

Threo-3-[5-chloro-2-[2-dimethylamino)ethyl] aminophenyl thio]-2-hydroxy -3-(4 -methoxyphenyl) propionic acid ($IV_T$e) (355 mg, 0.835 mmol) is acetylated in a similar manner to that described in Example 8 to obtain 2-acetoxy intermediate ($V_T$e) (386 mg, yield=99.0%) in an amorphous form.

IRvmax($CHCl_3$) ($cm^{-1}$) :3352,2426,1735,1609.

NMR($CDCl_3$) δ:2.21 (3H, S),2.82(6H,S),3 .35 (4H,m), 3.82(3H,S), 4.26 (1H,d,J=2.0), 5.22 (1H,d,J=2.0), 5.77 (2H), 6.46 (1H,d, J=8.6) 6.85 (2H,d,J=9.0), 7.08 (1H,d,J=2.4), 7.15 (1H,d,d,J=2.4, 8.6), 7.32 (2H,d,J=9.0).

Reference example 5

Erythro-3-[5-chloro-2-[2-(dimethylamino)ethyl] aminophenylthio]-2-hydroxy-3-(4-methoxyphenyl)propionic acid ($IV_E$e) (233 mg, 0.548 mmol) is acetylated in a similar manner to that described in Example 8 to obtain 2-acetoxy intermediate ($V_E$e) (232 mg, yield=90.6%) in an amorphous form.

IRvmax($CHCl_3$)($cm^{-1}$):3322,2394,1611.

NMR ($CDCl_3$) δ:1.85 (3H, S), 2.82 (6H, S), 3.39 (4H, m), 3.80 (3H, S), 4.12 (1H, d,J=10.8), 5.24 (1H,d,J=10.8), 6.02 (2H), 6.44 (1H,d, J=8.6),6.81 (2H,d,J=8.8),6.94 (1H,d,J= 2.6), 7.07 (2H, d,J=8.8), 7.13 (1H,d,d,J=2.6,8.6).

Step (4) in the process of the present invention is illustrated in the following Examples 13–17.

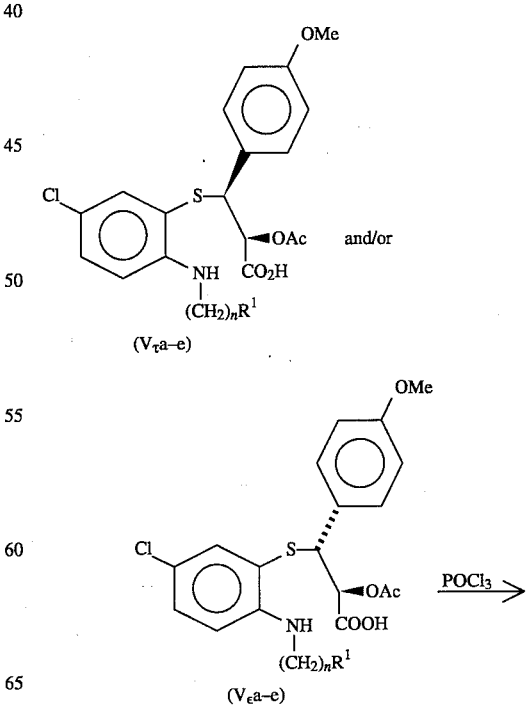

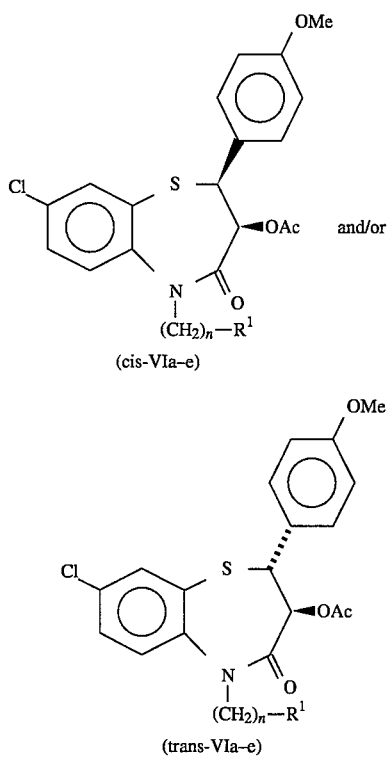

(cis-VIa-e)

(trans-VIa-e)

Example 13: Step (4)-a

A solution of threo-2-acetoxy-3-[5-chloro-2-[3-[4-(2-methoxyphenyl)piperazin-1-yl]propyl]aminophenylthio]-3-(4-methoxyphenyl) propionic acid ($V_T$a) (117 mg, 0.2 mmol) and pyridine (39 μl, 0.482 mmol) in dichloromethane (4 ml) is cooled to −30° C. and a solution of phosphorus oxychloride (121 μl, 0.225 mmol) in dichloromethane (4 ml) is added dropwise over 5 minutes. The resulting reaction mixture is stirred under ice-cooling for 1 hour, poured into ice water and extracted with ethyl acetate. The layer of ethyl acetate is washed with an aqueous solution of NaHCO$_3$ and a saturated saline solution and dried over MgSO$_4$. The resulting crude product (109 mg) is recrystallized from ethyl acetate/hexane to obtain (+)-cis-3-acetoxy-8-chloro- 2,3-dihydro-2-(4-methoxyphenyl)-5-[3-[4-(2-methoxyphenyl)piperazin- 1-yl]propyl-1,5-benzothiazepine-4(5H)-one (cis-VIa) (87 mg, yield=75.7%) as colorless prism-shaped crystals. The purity of compound (cis-VIa) was determined by HPLC under the following conditions.

Column:COSMOSIL$_5$ C18 4.6×250 mm.

Mobile phase:acetonitrile/PICB-7 aqueous solution(50/50).

Flow rate:1.0 ml/min.

Detection:UV254 nm

Retention time:11.0 min

The optical purity of compound (cis-VIa) was determined by HPLC using a column for resolving optical isomers under the following conditions.

Column:CHIRALCEL OD 4.6×250 mm

Mobile phase:Hexane/Ethanol(90/10)

Flow rate:1.0 ml/min

Detection:UV246 nm

Retention time:13.6 min

The physicochemical values and spectral data of compound (cis-VIa) are shown below.

Melting point: 109°–111° C.

Optical rotation:+107.6°(c=1.018,Methanol)

Elemental analysis: $C_{32}H_{36}N_3O_5SCl$. Calculated:C, 62.99 ;H, 5.95 ;N, 6.89. Found:C, 63.02;H, 6.03;N, 6.96.

IRvmax (CHCl$_3$) (cm$^{-1}$) :3340,2392,1736,1608.

NMR(CDCl$_3$) δ:2.22 (2H,m),2.20 (3H,S),2.70–3.60 (12H,m),3.73 (2H), 3.80 (3H,S), 3.87 (3H,S), 4.49 (1H, d,J=2.0), 5.31 (1H,d, J=2.0), 6.45 (1H, d,J=8.6), 6.76–7.15 (8H,m), 7.33 (2H, d,J=8.6)

Compound (cis-VIa) (3.5 g, 5.736 mmol) and citric acid (1.205 g, 5.737 mmol) are dissolved in ethanol (30 ml) to obtain the citrate (4.366 g, yield=94.9%) as colorless prism-shaped crystals.

Melting point: 179°–182° C.

Specific rotation: $[\alpha]_D^{23}$=+65.0±1.0 (c=1.007,Methanol)

Elemental analysis: $C_{32}H_{36}N_3O_5SCl \cdot C_6H_8O_7$. Calculated: C, 56.88 ;H, 5.52 ;N, 5.23. Found: C, 56.75 ;H, 5.54 ;N, 5.35.

IRvmax (nujol) (cm$^{-1}$): 3430,2620,1737,1674.

NMR(DMSO-d$_6$) δ:1.79 (2H,m),1.84 (3H,S),2.56–3.82, 4.20–4.32 (17H,m),3.76 (3H,S),3.78 (3H,S), 5.04 (1H,d,J= 8.2), 5.21 (1H,d, J=8.2), 6.80–7.86 (11H,m), 10.78 (3H).

Reference example 6

A solution of erythro-2-acetoxy-3-[5-chloro-2-[3-[4-(2-methoxyphenyl)piperazin-1-yl]propyl]aminophenyl thio]-3-( 4-methoxyphenyl)propionic acid ($V_E$a) (2.189 mg, 3.484 mmol) and pyridine (1.44 ml, 17.804 mmol) in dichloromethane (16 ml) was cooled to −30° C. and 1N solution of phosphorus oxychloride in dichloromethane (4.27 ml) was added over 10 minutes. The resulting reaction mixture was stirred under ice-cooling for 1 hour, poured into ice water, and extracted with ethyl acetate. The organic layer was washed with an aqueous solution of sodium bicarbonate and a saturated saline solution, and dried over MgSO$_4$ to obtain the crude product (2.036 g), which was converted to its oxalate. The oxalate was recrystallized from ethanol to obtain the oxalate (2.127 g, yield=87.1%, m.p. 155°~ 158° C.) as pale yellow prism-shaped crystals. Subsequently the oxalate (1.312 g) was neutralized with an aqueous solution of bicarbonate and extracted with ethyl acetate. The organic layer was dried over MgSO$_4$ and free-base compound (trans-VIa) (1.138 g, yield=99.6%) was obtained. Compound (trans-VIa) (1.138 g) was treated with citric acid (392 mg, 1.865 mmol) to give a citrate. The resulting citrate was recrystallized from methanol to obtain (+)-trans- 3-acetoxy-8-chloro -2,3-dihydro-2-(4-methoxyphenyl)-5-[ 3-[4-(2-methoxyphenyl)piperazin-1-yl]propyl-1,5-benzothiazepine-4(5H)-one citrate (1.432 g, yield=95.4%) as colorless prism-shaped crystals.

Melting point: 191°–192° C.

Specific rotation: $[\alpha]_D^{23}$=+275.8°(c=1.006,Methanol).

Elemental analysis: $C_{32}H_{36}N_3O_5SCl \cdot C_6H_8O_7$. Calculated: C, 56.88 ;H, 5.52 ;N, 5.23. Found: C, 57.02 ;H, 5.63 ;N, 5.46.

IRvmax(nujol) (cm$^{-1}$) :3446,2542,1736,1640.

NMR (DMSO-d$_6$) δ:1.75 (2H,m), 1.87 (3H, S), 2.55–3 . 68,4.05– 4.33 (16H,m), 2.61 (2H, S), 2.65 (2H, S), 3.74 (3H, S), 3.77 (3H, S), 4.86 (1H,d,j=11.0),4.99(1H,d,J=11.0), 6.80–7.86(11H,m).

Example 14: Step (4)-b

2-Acetoxy-3-[5-chloro -2-[3-(4-phenylpiperazin-1-yl)propyl]aminophenylthio]-3-(4-methoxyphenyl)propionic acid ($V_Tb+V_Eb$, threo/erythro=8.61/1) (2.006 g, 3.353 mmol) is subjected to a ring closure reaction in a similar manner to that described in Example 13 to obtain crude product (cis-VIb +trans-VIb) (1.941 g). This crude product is converted to its oxalate, which is recrystallized to obtain oxalate of (+)-cis-3-acetoxy-8-chloro-2,3-dihydro-2-(4-methoxyphenyl)- 5-[3-phenylpiperazin-1-yl]propyl -1,5-benzothiazepine- 4(5H)-one (cis-VIb) (1. 298 g, yield= 48.4%) as colorless prism-shaped crystals.

Melting point: 185°–188° C.

Specific rotation: $[\alpha]_D^{23}$=+74.2°(c=1.005, Methanol)

Elemental analysis: $C_{31}H_{34}N_3O_4 5Cl.C_2H_2O_4$. Calculated: C, 59.14 ;H, 5.41 ;N, 6.27. Found: C, 58.92 ;H, 5.51 ;N, 6.42.

IRvmax(nujol) (cm$^{-1}$) :3482,3352,2594,1758,1688.

NMR (DMSO-d$_6$) δ: 1.85 (2H,m), 1.84 (3H, S), 2.75–3.75,4.18–4.42 (12H,m),3.78(3H, S),5.04(1H,d,J= 7.4),5.20(1H, d,J=7.4),5.62 (2H), 6.75–7.87 (12H,m).

Example 15: Step (4)-c

Threo-2-acetoxy-3-[5-chloro-2-[3-[4-(4-methylphenyl)piperazin-1-yl]propyl]aminophenylthio]-3-(4-methoxyphenyl) propionic acid ($V_Tc$) (722 mg, 1.179 mmol) is subjected to a ring closure reaction in a similar manner to that described in Example 13 to obtain crude product (711 mg). This product is recrystallized from ethyl acetate/hexane to obtain (+)-cis-3-acetoxy-8-chloro-2,3-dihydro-2-(4-methoxyphenyl)- 5-[3-[4-(4-methylphenyl)piperazin-1-yl]propyl] -1,5-benzothiazepine-4(5H)-one (cis-VIc) (588 mg, yield=84.0%) as colorless prism-shaped crystals.

Melting point:118°–120° C.

Specific rotation: $[\alpha]_D^{24}$=+109.0° (c=1.008,Methanol).

Elemental analysis: $C_{32}H_{36}N_3O_4SCl$. Calculated: C, 64.69 ;H, 6.11 ;N, 7.07. Found: C, 64.47;H, 6.13 ;N, 7.06.

IRvmax(nujol) (cm$^{-1}$) :1746,1678.

NMR(CDCl$_3$) δ:1.83 (2H,m),1.91 (3H,S),2.26 (3H,S), 2.54 (6H,m), 3.1 (4H, m), 3.63 (1H,m), 4.49 (1H,m), 3.82 (3H, S), 5.03 (1H, d, J=7.6) 5.15(1H,d,J=7.6), 6.78–7.55(11H,m).

EXAMPLE 16: Step (4)-d

2-Acetoxy-3-[S-chloro-2-[3-(4-benzhydrylpiperazin-1-yl) propyl]aminophenylthio]-3-(4-methoxyphenyl)propionic acid ($V_Td+V_Ed$, threo/erythro=4.75/1) (3.352 g, 4.87 mmol) is subjected to a ring closure reaction in a similar manner to that described in Example 13 to obtain crude product (cis-VId+trans-VId) (3.196 g, yield=90.0%). The crude product is subjected to column chromatography on silica gel. The eluate eluted with ethyl acetate is converted to its hydrochloride. The hydrochloride is washed with ethyl ether to obtain hydrochloride of (+)-cis- 3-acetoxy-S-chloro-2,3-dihydro-5-[3-(4-benzhydrylpiperazin- 1-yl]propyl-2-(4-methoxyphenyl)-1,5-benzothiazepine-4(5H)-one (cis-VId) (2.1 g, yield=57.8%) in an pale yellow colored amorphous form.

Specific rotation: $[\alpha]_D^{26}$=+64.2° (c=1.005,Methanol)

Elemental analysis: $C_{38}H_{40}N_3O_4SCl.1.8HCl.\frac{1}{2}H_2O$. Calculated:C, 61.26 ;H, 5.82 ;N, 5.64. Found:C, 60.95;H, 5.91;N, 5.59.

IRvmax (CHCl$_3$) (cm$^{-1}$): 3410,2392,1676 NMR(CDCl$_3$)δ:1.88 (3H,S),2.26 (2H,m),3.13–4.99 (13H, m),3.82 (3H,S), 5.0 (1H,d,J=7.8), 5.08 (1H, d,J=7.8), 6.77–8.10 (17H,m), 13 .04 (mH), 13.71 (mH).

Example 17: Step (4)-e

Threo-2-acetoxy-3-[5-chloro-2-[(2-dimethylamino) ethyl] aminophenylthio]-3-(4-methoxyphenyl)propionic acid ($V_Te$) (390 mg, 0.835 mmol) is subjected to a ring closure reaction in a similar manner to that described in Example 13 to obtain crude product (363 mg). The crude product is converted to maleate, which is recrystallized from ethanol to obtain maleate of (+)-cis-3-acetoxy-8-chloro-2,3-dihydro- 5-[2-(2-dimethylamino) ethyl]-2-(4-methoxyphenyl)- 1,5-benzothiazepine-4 (SH)-one (cis-VIe) (368 mg, yield= 78.0%) as colorless needle-shaped crystals.

Melting point: 159°–160° C.

Specific rotation: $[\alpha]_D^{25}$=+75.1° (c=1.006,Methanol)

Elemental analysis: $C_{22}H_{25}N_2O_4SCl.C_4H_4O_4$. Calculated:C, 55.27 ;H, 5.17 ;N, 4.96. Found:C,55.40;H,5.29;N, 5.00.

IRvmax(nujol)(cm$^{-1}$):2616,2410,1752,1684.

NMR (CDCl$_3$) δ:1.92 (3H, S), 2.90 (6H, S), 3.37 (2H, m), 3.83 (3H, S), 4.33 (2H,m), 5.03 (1H,d,J=7.8), 5.10 (1H,d, j=7.8), 6.27 (2H,S), 6.91 (2H,d,J=9.0), 7.36 (2H,d,J=9.0), 7.41 (1H,d,J=8.6), 7.56 (1H d,d,J=2.4,8.6), 7.74 (1H,d,J= 2.4).

Reference example 7

Erythro-2-acetoxy-3-[5-chloro-2-[(2-dimethylamino) ethyl]aminophenylthio]-3-(4-methoxyphenyl) propionic acid ($V_Ee$) (232 mg, 0.5 mmol) was subjected to a ring closure reaction in a similar manner to that described in Example 13 to obtain crude product (206 mg). The crude product was converted to maleate, which is recrystallized from ethanol maleate of (+)-trans-3-acetoxy-8-chloro-2,3-dihydro- 5-[2-(2-dimethylamino) ethyl]-2-(4-methoxyphenyl)- 1,5-benzothiazepine-4 (5H)-one (trans-VIe) (155 mg, yield= 59.4%) as colorless needle-shaped crystals.

Melting point: 151°–152° C.

Specific rotation: $[\alpha]_D^{25}$=+391.5° (c=1.016,Methanol)

Elemental analysis: $C_{22}H_{25}N_2O_4SCl.C_4H_4O_4$. Calculated: C, 55.22 ;H, 5.20 ;N, 4.96. Found: C, 54.93 ;H, 5.28 ;N, 4.95.

IRvmax(nujol) (cm$^{-1}$) :3578,3500,2660,1738,1692.

NMR(CDCl$_3$)δ:1.95(3H,S),2.88(6H,S),3.32(2H,m), 3.80(3H, S), 4.29 (2H,m), 4.53 (1H,d,J=11.0), 5.01 (1H,d, J=11.0), 6.27 (2H, S), 6.85(2H,d,J=8.6),7.02(2H,d,J=8.6), 7.55(3H,m).

The syntheses of starting compounds (Ia~e) for the process of the present invention based on the above Reaction scheme 4 are shown in the following reference examples 8~18.

Reference example 8

6-chloro-3-(3-chloropropyl)-2-benzothiazolone (X)

A solution of 6-chloro-benzothiazolone (VIII) (55.7 g, 0.3 mol), $K_2CO_3$ (62.1 g, 0.45 mol) and 1-bromo-3-chloropropane (IX) (71 g, 0.45 mol) in acetone (600 ml) was refluxed for 16 hours. After cooling, the inorganic substance was filtered off and washed dichloromethane. The filtrate and washings were combined and evaporated in vacuo. The residue was washed with hexane and recrystallized from dichloromethane to obtain compound (X) (73.5 g, yield= 93.4%) as colorless needle-shaped crystals.

Melting point:131°–132° C.

Elemental analysis:$C_{10}H_9NOSCl_2$. Calculated:C, 45.82;H,3.46;N,5.34. Found:C,45.56;H,3.50;N,5.41.

IRvmax (nujol) ($cm^{-1}$): 1673,1162.

NMR($CDCl_3$) δ:2.21 (2H,quint,J=6.2),3.61 (2H, t,J=6.2), 4.11 (2H,t,J=7.0),7.08(1H, d,J=8.6),7.32(1H,d,d,J=8.6,2.0), 7.43 (1H,d,J=2.0).

Reference example 9

6-chloro-3-[3-[4: (2-methoxyphenyl)piperazin-1-yl]propyl]-2-benzothiazolone (XIIa)

A solution of compound (X) (73.4 g, 0.28 tool), $K_2CO_3$ (85.2 g, 0.62 mol), 1-(2-methoxyphenyl)piperazine hydrochloride (XIa) (70.44 g, 0.31 mol), and KI (46.7 g, 0.28 mol) in DMF (500 ml) was stirred at 110° C. for 2 hours. After cooling, inorganic substance was filtered off and washed with ethyl acetate. The filtrate and washings were combined and evaporated in vacuo. The residue was recrystallized from EtOH (400 ml). The crystals were filtered off, washed with water and ethanol and recrystallized from ethanol to obtain compound (XIIa) (107.8 g, yield=92%) as colorless needle-shaped crystals.

Melting point: 120°–121° C.

Elemental analysis: $C_{21}H_{24}N_3O_2SCl$. Calculated: C, 60.35 ;H, 5.79 ;N, 10.06. Found: C, 60.39 ;H, 5.77 ;N, 10.19.

IRvmax (nujol) ($cm^{-1}$): 1684,1183.

NMR($CDCl_3$) δ:1.97(2H,quint,J=6.8),2.48 (2H,t,J=6.8), 2.63 (4H,m), 3.08 (4H,m), 3.86 (3H, S), 4.04 (2H, t,J=6.8), 6.95 (4H,m), 7.16 (1H,d,J=8.8),7.28(1H,d,d,J=8.8,2.2), 7.42(1H,d,J=2.2).

Reference example 10

6-chloro-3-[3-(4phenylpiperazin-1-yl)propyl]-2-benzothiazolone (xIIb)

A solution of compound (X) (3.71 g, 20 mmol), $K_2CO_3$ (3.31 g, 24 tool), phenylpiperazine (XIb) (3.24 g, 20 mmol), and KI (3.98 g, 24 mmol) in DMF (20 ml) was stirred at 100° C. for 5 hours and concentrated in vacuo. The residue was extracted with dichloromethane, washed with a saturated saline solution and dried over $MgSO_4$. The dichloromethane layer was subjected to column chromatography on silica gel. The eluate eluted with dichloromethane/ethyl acetate (4/1) was recrystallized from ethyl ether to obtain compound (XIIb) (4.8 g, yield=61.9%) as colorless prism-shaped crystals.

Melting point: 126°–127° C.

Elemental analysis: $C_{20}H_{22}N_3OSCl$. Calculated: C, 61.93 ;H, 5.72 ;N, 10.83. Found:C, 61.83 ;H, 5.78;N, 10.90.

IRvmax (nujol) ($cm^{-1}$): 1680,1177.

NMR ($CDCl_3$) δ: 1.97 (2H, quint, J=6.8), 2.46 (2H, t, J=6.8), 2.58 (4H,m), 3.19 (4H,m), 4.04 (2H,t,J=6.8), 6.88 (3H,m), 7.13 (1H,d, J=8.6), 7.28(3H,m),7.41(1H,d,J=2.0).

Reference example 11

6-chloro-3-[3-(4-methylphenyl) piperazin-1-yl]propyl]-2-benzothiazolone (XIIc)

A solution of compound (X) (3.71 g, 20 mmol), $K_2CO_3$ (4.97 g, 36 tool), 4-(4-methylphenyl)piperazine hydrochloride (XIc) (5.98 g, 24 mmol), and KI (3.98 g, 24 mmol) in DMF (20 ml) was stirred at 100° C. for 5 hours, concentrated in vacuo and filtered. The resulting crystals were washed with water and recrystallized from isopropyl ether to obtain compound (XIIc) (5.1 g, yield=63.7%) as colorless needle-shaped crystals.

Melting point: 125°–126° C.

Elemental analysis: $C_{21}H_{24}N_3OSCl$. Calculated: C, 62.76; H, 6.02 ;N, 10.46. Found: C, 62.54 ;H, 6.05 ;N, 10.63.

IRvmax(nujol) ($cm^{-1}$) :1681,1185.

NMR ($CDCl_3$) δ:1.95 (2H, quint, J=6.8), 2.27 (3H, S), 2.45 (2H, t, J=6.8), 2.57 (4H,m), 3.13 (4H,m), 4.03 (2H, t,J=7.0), 6.84 (2H,d, J=8.6), 7.08 (2H, d,J=8.6), 7.13 (1H, d,J=8.6), 7.27 (1H, d, d,J=8.6, 2.0), 7.41 (1H,d,J=2.0).

Reference example 12

6-chloro-3-[3-(4-benzhydrylpiperazin-1-yl]propyl]-2-benzothiazolone (XIId)

A solution of compound (X) (3.71 g, 20 mmol), $K_2CO_3$ (3.31 g, 24 mmol), 4-benzhydrylpiperazine (XId) (6.06 g, 24 mmol), and KI (3.98 g, 24 mmol) in DMF (20 ml) was stirred at 100° C. for 5 hours, concentrated in vacuo and extracted with dichloromethane. The resulting dichloromethane layer was dried over $MgSO_4$, and subjected to column chromatography on silica gel. The eluate eluted with dichloromethane/ethyl acetate (10/1) was recrystallized from ether to obtain compound (XIId) (5.9 g, yield=61.7% ) as colorless prism-shaped crystals.

Melting point:130°–132° C.

Elemental analysis:$C_{27}H_{28}N_3OSCl$. Calculated:C, 67.84;H,5.90;N,8.79. Found:C,67.75;H,6.04;N,8.92.

IRvmax(nujol)($cm^{-1}$):1678,1160.

NMR ($CDCl_3$) δ: 1.88 (2H, quint, J=6.8), 2.37 (2H, t, J=6.8), 2.40 (8H,m), 3.97 (2H, t,J=6.8), 4.22 (1H, S), 7.1 (1H,d,J=8.6), 7.25 (11H,m), 7.42 (1H,d,J=1.8).

Reference example 13

6-chloro-3-[2-(dimethylamino)ethyl]-2-benzothiazolone (XIIe)

A solution of compound (VIII) (9.28 g, 50 mmol), N,N-dimethylaminoethylchloride hydrochloride (XIe) (7.92 g, 55 mmol), and $K_2CO_3$ (16.58 g, 120 mmol) in acetone (93 ml) was refluxed for 20 hours with stirring. After the reaction was complete, the reaction mixture was concentrated in vacuo. The residue was extracted with ethyl acetate. The layer of ethyl acetate was dried over $MgSO_4$ and subjected to column chromatography on silica gel. From the eluate eluted with ethyl acetate, compound (XIIe) (3.3 g, yield= 64.3%) was obtained as an oil.

IRvmax(nujol)($cm^{-1}$):1680,1168.

NMR ($CDCl_3$)δ:2.31 (6H, S), 2.59 (2H, t, J=7.2), 4.03 (2H, t, J=7.2), 7.01(1H,d,J=8.6),7.29(1H,d,d,J=8.6,2.2), 7.41(1H,d,J=2.2).

Reference example 14

5-chloro-2-[3-[4-(2-(methoxyphenyl)piperazin-1-yl]propyl]-aminobenzenethiol (Ia)

To a solution of compound (XIIa) (12.54 g, 30 mmol) in ethanol (76 ml) was added a solution of KOH (8.42 g, 150 mmol) in water (8.4 ml). The mixture was refluxed in a stream of nitrogen for 4 hours. The ethanol was distilled away in vacuo. The residue was cooled and ice water (70 g) was added. The resulting liquid was neutralized to pH 4.49 with an excess of acetic acid (30 ml). The precipitated crystals were filtered off, washed with water until the smell of acetic acid completely disappeared, and then washed with methanol (20 ml) and ether (30 ml), and dried in vacuo overnight to obtain pale yellow powder like crystals (Ia) (10.95 g, yield=91.9%).

Purity: 96.0% (HPLC).

Melting point: 137°–142° C.

Elemental analysis:$C_{20}H_{26}N_3OSCl$.

Calculated:C,61.22;H,6.63;N,10.71.

Found:C,60.93;H,6.73;N,10.67.

IRvmax(nujol) (cm$^{-1}$) :3246,2522.

NMR(CDCl$_3$)δ:1.91(2H,t,J=6.4),2.59(2H, t,J=6.4)2.73, 3.14 (8H,m),2.95(NH,SH),3.24(2H, t,J=6.4),3.87(3H,S), 6.5–7.37(7H, m).

HPLC condition:

Column:COSMOSIL$_5$ C18 4.6×150 mm

Mobile phase:acetonitrile/PICB-7 aqueous solution(50/50)

Flow rate:1.0 ml/min

Detection:IB7254 nm

Retention time:6.2 min

Reference example 15

5-chloro-2-[3-(4-phenylpiperazin-1-yl)propyl]aminobenzenethiol (Ib)

Compound (XIIb) (1.94 g, 5 mmol) was treated in a similar manner to that described in Reference example 14 to obtain pale yellow powder-like crystals (Ib) (1.746 g, yield=96.5%).

Purity:93.6%(HPLC)

Melting point:135°–145° C.

Elemental analysis:$C_{19}H_{24}N_3SCl$. Calculated:C,62.78;H, 6.63;N,11.60. Found: C, 62.35 ;H, 6.71 ;N, 11.47.

IRvmax (nujol) (cm$^{-1}$): 3250,2150.

NMR (CDCl$_3$)δ:1.98 (2H, quint, J=6.6), 2.10 (NH, SH), 2.67 (2H, t, J=6.6), 2.77 (4H,m), 3.15–3.40 (6H,m), 6.56 (1H,d,J=9.0), 6.83–7.4 0 (7H,m).

Reference example 16

5-chloro-2-[3-[4-methylphenyl)piperazin-1-yl]propyl]aminobenzenethiol

Compound (XIIc) (2.128 g, 5.294 mmol) was treated in a similar manner to that described in Reference example 14 to obtain pale yellow powder-like crystals (Ic) (1.872 yield=94.1%).

Purity: 96.3% (HPLC)

Melting point: 137°–147° C.

Elemental analysis :$C_{20}H_{26}N_3SCl \cdot \frac{1}{2}H_2O$. Calculated: C, 62.43 ;H, 7.01 ;N, 10.91. Found:C, 62.84 ;H, 6.81 ;N, 11.00.

IRvmax(nujol) (cm$^{-1}$) :3362,2318.

NMR (CDCl$_3$)δ:1.97 (2H, quint, J=6.6), 2.28 (3H, S), 2.45 (NH, SH), 2.66 (2H, t, J=6.6), 2.77 (4H, m), 3.11–3.34 (6H, m), 6.53 (1H, d, J=8.6), 6.80–7.37 (6H,m).

Reference example 17

5-chloro-2-[3-(4-benzhydrylpiperazin-1-yl)propyl]-aminobenzenethiol (Id)

Compound (XIId) (2.87 g, 6.004 mmol) was treated in a similar manner to that described in Reference example 14 to obtain pale yellow powder-like crystals (Id) (2.584 g, yield=95.2%).

Purity: 90.7% (HPLC)

Melting point: 142°–150° C.

IRvmax(nujol) (cm$^{-1}$) :3260,2336.

NMR (CDCl$_3$) δ:1.84 (2H, t, J=6.2), 2.15 (NH, SH), 2.35–2.65 (8H,m), 2.52 (2H, t,J=6.2), 3.18 (2H, t,J=6.2), 4.25 (1H,S), 6.49 (1H, d, J=9.0), 7.05–7.47 (12H,m).

Reference example 18

5-chloro-2-[2-(dimethylamino)ethyl]aminobenzenethiol (Ie)

Compound (XIIe) (3.825 g, 14.898 mmol) was treated in a similar manner to that described in Reference example 14 to obtain pale yellow powder-like crystals (Ie) (1.617 g, yield=47.0%).

Purity:92.7%(HPLC)

Melting point:135°–140° C.

Elemental analysis:$C_{10}H_{15}N_2SCl$. Calculated:C,52.05;H, 6.55;N,12.14. Found:C,51.73;H,6.52;N,12.23.

IRvmax(nujol)(cm$^{-1}$):3230,2156.

NMR (CDCl$_3$)δ:2.32 (6H, S), 2.63 (2H, t ,J=6.0), 3.21 (2H, t ,J=6.0), 3.26(NH, SH),6.53((1H,d,J=8.6),7.11(1H, d,d, ,J=2.6,8.6),7.37 (1H,d,J=2.6).

What is claimed is:

1. A process for stereoselectively preparing a threo-form of a compound represented by formula (III)

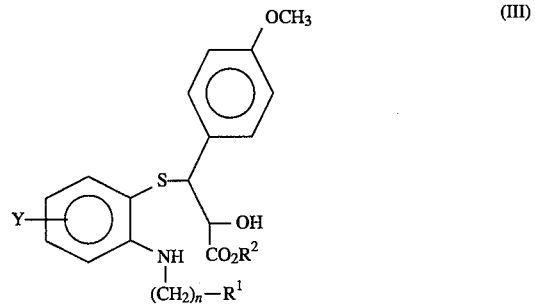

wherein

Y represents a member selected from the group consisting of hydrogen, halogen, $C_1$–$C_6$ alkyl, $C_3$–$C_6$ cycloalkyl, $C_1$–$C_6$ alkoxy, aryl, aryl $C_1$–$C_6$ alkyl, aryl $C_1$–$C_6$ alkoxy and aryloxy, the aryl portion of such groups being phenyl or naphthyl, n is an integer of 1–6, $R^1$ represents an amino group represented by the formula:

—NR$^{1a}$R$^{1b}$ wherein (1) $R^1$ and $R^2$ each independently represents hydrogen or straight or branched $C_1$–$C_6$ alkyl, or (2) $R^{1a}$ and $R^{1b}$ may form, taken together with the nitrogen to which $R^{1a}$ and $R^{1b}$ are attached, a cyclic amino group selected from the group consisting of 1-piperazinyl, 1-piperidyl, 1-pyrrolidinyl, 4-morpholinyl and 4-thiomorpholinyl, said cyclic amino groups being unsubstituted or substituted by unsubstituted or substituted phenyl, $C_1$–$C_6$ alkyl, unsubstituted or substituted phenylalkyl or unsubstituted or substituted diphenylalkyl, the substituents on the substituted phenyl, substituted phenylalkyl and substituted diphenylalkyl being halogen, $C_1$–$C_6$ alkyl, $C_1$–$C_6$ alkoxy or methylenedioxy and the alkyl portion of said groups being $C_1$–$C_6$ alkyl, and $R^2$ represents lower alkyl, said process comprising reacting an o-(aminoalkylamino) thiophenol compound represented by formula (I):

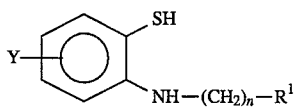

wherein Y, D and $R^1$ are as defined above with an ester of trans-3-(4-methoxyphenyl)glicidic acid represented by formula (II):

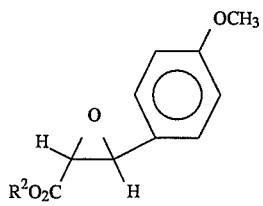

wherein $R^2$ is as defined above, at an elevated temperature in a nonpolar solvent in the presence of a divalent or trivalent iron ion.

2. A process for stereoselectively preparing a cis-form of 1,5-benzothiazepine derivative represented by formula (VI):

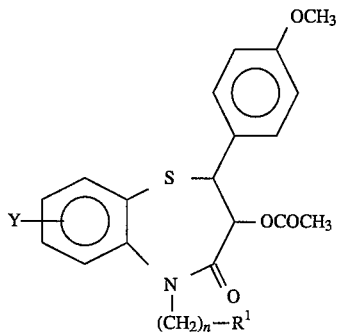

wherein

Y represents a member selected from the group consisting of hydrogen, halogen, $C_1$–$C_6$ alkyl, $C_3$–$C_6$ cycloalkyl, $C_1$–$C_6$ alkoxy, aryl, aryl $C_1$–$C_6$ alkyl, aryl $C_1$–$C_6$ alkoxy and aryloxy, the aryl portion of such groups being phenyl or naphthyl, n is an integer of 1–6, and $R^1$ represents an amino group represented by the formula:

wherein (1) $R^{1a}$ and $R^{1b}$ each independently represents hydrogen or straight or branched $C_1$–$C_6$ alkyl, or (2) $R^{1a}$ and $R^{1b}$ may form, taken together with the nitrogen to which $R^{1a}$ and $R^{1b}$ are attached, a cyclic amino group selected from the group consisting of 1-piperazinyl, 1-piperidyl, 1-pyrrolidinyl, 4-morpholinyl and 4-thiomorpholinyl, said cyclic amino groups being unsubstituted or substituted by unsubstituted or substituted phenyl, $C_1$–$C_6$ alkyl, unsubstituted or substituted phenylalkyl or unsubstituted or substituted diphenylalkyl, the substituents on the substituted phenyl, substituted phenylalkyl and substituted diphenylalkyl being halogen, $C_1$–$C_6$ alkyl, $C_1$–$C_6$ alkoxy or methylenedioxy and the alkyl portion of said groups being $C_1$–$C_6$ alkyl, the process comprising, (1) stereoselectively preparing a threo-form of a compound represented by formula (III):

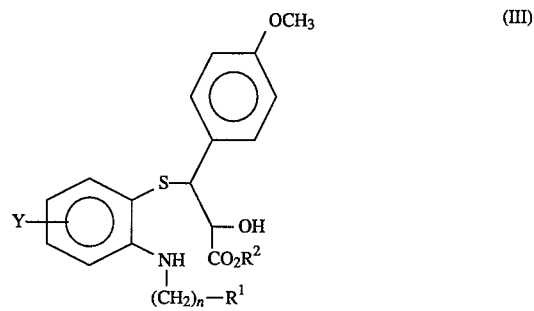

by reacting an o-(aminoalkylamino) thiophenol compound represented by formula (I):

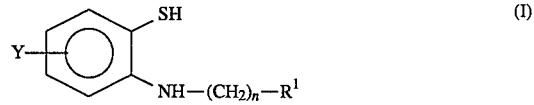

wherein Y, n and $R^1$ are as defined above, with a trans-3-(4-methoxyphenyl)glicidic ester represented by formula (II):

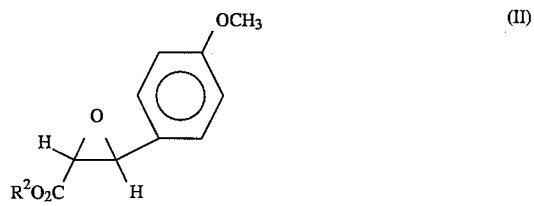

wherein $R^2$ represents lower alkyl, at an elevated temperature in a nonpolar solvent in the presence of a divalent or trivalent iron ion;

(2) hydrolysing the ester group of the compound obtained in Step (1) to yield a carboxylic acid represented by formula (IV):

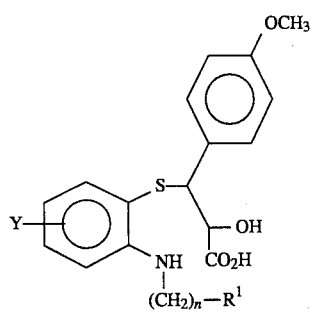

(IV)

(3) acetylating the 2-hydroxyl group of the carboxylic acid obtained in Step (2) to convert it into a 2-acetoxy compound represented by formula (V):

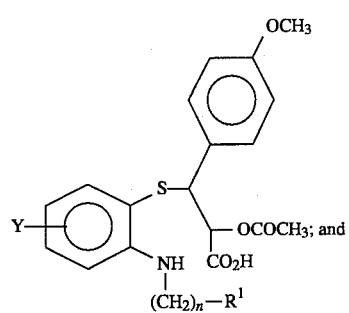

(V)

(4) subjecting the 2-acetoxy compound obtained in step (3) to a ring closure reaction to convert it into a 1,5-benzothiazepine derivative represented by formula (VI).

3. A process as claimed in claim 2 wherein said trivalent iron ion is that derived from iron (III) hydroxide oxide.

4. A process as claimed in claim 1 wherein said nonpolar solvent is xylene.

5. A process as claimed in claim 1 wherein said trivalent iron ion is that derived from iron (III) hydroxide oxide.

6. A process as claimed in claim 2 wherein said nonpolar solvent is xylene.

* * * * *